(12) United States Patent
Ito et al.

(10) Patent No.: US 11,493,393 B2
(45) Date of Patent: Nov. 8, 2022

(54) IN-SITU STRESS MEASUREMENT METHOD

(71) Applicants: Japan Petroleum Exploration Co., Ltd., Tokyo (JP); Tohoku University, Sendai (JP)

(72) Inventors: Takatoshi Ito, Sendai (JP); Kazuhiko Tezuka, Ichihara (JP); Tetsuya Tamagawa, Chiba (JP)

(73) Assignees: JAPAN PETROLEUM EXPLORATION CO., LTD., Tokyo (JP); TOHOKU UNIVERSITY, Sendai (JP)

( * ) Notice: Subject to any disclaimer, the term of this patent is extended or adjusted under 35 U.S.C. 154(b) by 695 days.

(21) Appl. No.: 16/473,407

(22) PCT Filed: Nov. 6, 2017

(86) PCT No.: PCT/JP2017/039889
§ 371 (c)(1),
(2) Date: Jun. 25, 2019

(87) PCT Pub. No.: WO2018/123269
PCT Pub. Date: Jul. 5, 2018

(65) Prior Publication Data
US 2020/0149984 A1    May 14, 2020

(30) Foreign Application Priority Data
Dec. 27, 2016 (JP) .............................. JP2016-254104

(51) Int. Cl.
*G01L 5/00* (2006.01)
*E21B 49/00* (2006.01)
(Continued)

(52) U.S. Cl.
CPC .............. *G01L 5/00* (2013.01); *E21B 49/006* (2013.01); *E21B 49/06* (2013.01); *G01L 1/00* (2013.01)

(58) Field of Classification Search
USPC ........................................................... 702/6
See application file for complete search history.

(56) References Cited

U.S. PATENT DOCUMENTS

| | | | |
|---|---|---|---|
| 4,491,022 A | 1/1985 | de la Cruz | |
| 2009/0070042 A1* | 3/2009 | Birchwood | G01V 1/50 702/11 |

(Continued)

FOREIGN PATENT DOCUMENTS

| | | |
|---|---|---|
| JP | 2787752 B2 | 8/1998 |
| JP | 2004125672 A | 4/2004 |

OTHER PUBLICATIONS

Funato et al., "A new method of diametrical core deformation analysis for in-situ stress measurements," International Journal of Rock Mechanics & Mining Sciences, vol. 91, pp. 112-118 (2017).

(Continued)

*Primary Examiner* — Paul D Lee
(74) *Attorney, Agent, or Firm* — Panitch Schwarze Belisario & Nadel LLP

(57) ABSTRACT

An in-situ stress measurement method is provided. The method includes measuring a length of a maximum diameter at which an amount of distortion relative to a diameter of a standard circle of a measurement cross section of a boring core is largest and a length of a minimum diameter at which the amount of distortion relative to the diameter of the standard circle is smallest based on a shape of the measurement cross section of the boring core; measuring a length of a diameter in a vertical direction and a length of a diameter in a horizontal direction of the measurement cross section of a side-wall core acquired by hollowing ground in a well in (Continued)

an excavation direction thereof, based on a shape of the measurement cross section of the side-wall core; and calculating a maximum horizontal stress and a minimum horizontal stress by first and second equations.

8 Claims, 6 Drawing Sheets

(51) Int. Cl.
*E21B 49/06* (2006.01)
*G01L 1/00* (2006.01)

(56) References Cited

U.S. PATENT DOCUMENTS

| | | | |
|---|---|---|---|
| 2009/0133932 A1 | 5/2009 | Church | |
| 2010/0282516 A1* | 11/2010 | Buchanan | E21B 49/06 175/58 |
| 2015/0055438 A1* | 2/2015 | Yan | E21B 47/00 367/73 |
| 2017/0160429 A1* | 6/2017 | Berard | G01V 99/005 |

OTHER PUBLICATIONS

International Search Report dated Jan. 30, 2018 in International Application No. PCT/JP2017/039889.

* cited by examiner

IN-SITU STRESS MEASUREMENT METHOD

CROSS-REFERENCE TO RELATED APPLICATION

This application is a Section 371 of International Application No PCT/JP2017/039889, filed Nov. 6, 2017, which was published in the Japanese language on Jul. 5, 2018 under International Publication No. WO 2018/123269 A1, which claims priority under 35 U.S.C. § 119(b) to Japanese Application No. 2016-254104, filed Dec. 27, 2016, the disclosures of which are incorporated herein by reference in their entirety.

TECHNICAL FIELD

The present invention relates to a method for measuring a three-dimensional stress element acting on the ground configuring the earth's crust, that is, an in-situ stress measurement method.

BACKGROUND ART

In the mining of underground resources such as petroleum, natural gas, and the like, first, petroleum geological conditions are evaluated by remote sensing, aerial photographic interpretation, or the like, subsequently, the geological structure of the underground is inferred by comprehensively analyzing a plurality of data obtained by geological and geochemical investigations, seismic exploration, and the like, and a place in which a large amount of petroleum is highly likely to be found is selected. Once a candidate site of a petroleum gas well is selected, an exploratory well is excavated in the site, and the status of the geological layer is evaluated. When a geological layer in which petroleum is expected to be found in the ground in which the exploratory well has been excavated, the core of rock is mined from the ground including the geological layer, the type, mineral texture, and the like of the rock are acknowledged by observing the core, and, furthermore, the properties of the rock included in the geological layer such as porosity, penetration rate, or the like are investigated in detail.

For inference of the status of the ground of the candidate site, it is also important to analyze the mechanical behaviors of the ground such as consolidation, stresses in the ground, shear, earth pressure, and the like. When the stress state of the ground in which the petroleum gas well is excavated is evaluated on the basis of the analysis results and the fact that the petroleum gas well can be robustly maintained for a long period of time can be confirmed, it is possible to stably produce petroleum from the petroleum gas well.

The evaluation of the stress environment of the ground is carried out on explanatory wells, and is also carried out on petroleum gas wells intended for the continuous production of petroleum. When three-direction stresses can be accurately measured in such petroleum gas wells, it is possible to precisely acknowledge the dynamic environment around the tectonic ground, and thus it is possible to effectively carry out fracturing on the tectonic ground. As a result, it is possible to efficiently mine petroleum through fractures.

Patent Document 1 discloses a method for measuring three-dimensional stress elements acting on the ground configuring the earth's crust. Specifically, a petroleum gas well in which stresses in the earth's crust are to be measured changes the direction at least twice in the middle, the locations and angles of fissures in the wall of the well are measured at three places having different orientations, the main stresses, the orientations, and the inclinations of the three places are set respectively on the basis of the measurement values, a random three-dimensional crustal stress field is assumed, and the main stresses, the orientations, and the inclinations of the respective places are obtained using the values of the assumed random three-dimensional crustal stress field.

In addition, Non Patent Document 1 reports that it is possible to measure the degrees of three-direction stresses acting on the tectonic ground at a depth at which a boring core has been acquired by combining information obtained from the boring core and known information.

CITATION LIST

Patent Document

Patent Document 1: Japanese Patent No. 2787752

Non-Patent Document

Non Patent Document 1: "A new method of diametrical core deformation analysis for in-situ stress measurements" by Akio FUNATO and Takatoshi ITO, published in International Journal of Rock mechanics & Mining Sciences 91 (2017) 112 to 118 (http://www.sciencedirect.com/science/article/pii/S1365160916303690)

SUMMARY OF INVENTION

Technical Problem

In the invention of Patent Document 1, the well in which stresses in the earth's crust are to be measured needs to change the direction twice (there are three places having different orientations). However, wells do not necessarily change the orientation in the ground as described above, and, in a case where wells are dug vertically downwards, it is not possible to measure stresses by carrying out this invention. In addition, even when a well changes the orientation in the ground, it is difficult to say that sections having different orientations are sufficiently close to each other (the orientation of wells is not capable of abruptly changing, and thus the distance between the sections extends, and the depths thereof differ from each other), and thus it is difficult to say that the obtained numerical values of the stresses in the earth's crust are highly accurate.

In addition, in the report of Non Patent Document 1, there is an assumption that the boring core is acquired in advance, but boring cores are acquired in fragments during the excavation of wells, and thus the proposal of Non Patent Document 1 cannot be carried out in a case where there is no boring core acquired at a depth at which three-dimensional stresses need to be measured.

An object of the present invention is to provide an in-situ stress measurement method capable of precisely measuring three-dimensional stress elements acting on the ground configuring the earth's crust at any depths.

Solution to Problem

In a first aspect of an in-situ stress measurement method according to the present invention, the method includes:

measuring a length of a maximum diameter ($D_{max}$) at which an amount of distortion relative to a diameter of a standard circle of a measurement cross section of a cylindrical boring core is largest and a length of a minimum diameter ($D_{min}$) at which the amount of distortion relative to the diameter of the standard circle is smallest based on a shape of the measurement cross section of the boring core, wherein the boring core is acquired by hollowing ground in a well located at a predetermined depth from the earth's surface out in an excavation direction of the well, and the measurement cross section of the boring core is set in a direction orthogonal to a longitudinal direction of the boring core;

measuring a length of a diameter ($d1|_{\phi=0}$) in a vertical direction of a measurement cross section of a cylindrical first side-wall core and a length of a diameter ($d1|_{\phi=90}$) in a horizontal direction of the measurement cross section of the first side-wall core based on a shape of the measurement cross section of the first side-wall core, wherein the first side-wall core is acquired by hollowing the ground in the well located at the predetermined depth out from an inside surface of the well in a direction different from the excavation direction of the well, and the measurement cross section of the first side-wall core is set in a direction orthogonal to a longitudinal direction of the first side-wall core; and calculating a maximum horizontal stress ($S_{Hmax}$) and a minimum horizontal stress ($S_{hmin}$) among the three-dimensional stress elements by first and second equations, wherein the first equation represents a differential stress ($\Delta S$) between a maximum horizontal stress ($S_{Hmax}$) and a minimum horizontal stress ($S_{hmin}$) acting on the ground at the predetermined depth, $$\Delta S = S_{Hmax} - S_{hmin} = \frac{E}{1+v} \cdot \frac{D_{max} - D_{min}}{D_{min}}$$

the second equation represents a differential stress ($\Delta \sigma|_{\beta_1}$) between a horizontal stress ($\sigma_\theta$) and a vertical stress ($\sigma_v$) that act orthogonal to the longitudinal direction of the first side-wall core, $$\Delta \sigma|_{\beta_1} = \frac{1}{2}(S_{Hmax} + S_{hmin}) - \frac{1}{2}(S_{Hmax} - S_{hmin})\cos 2(\beta_1 - \alpha) - S_V = \frac{E}{1+v} \cdot \frac{d1|_{\phi=90} - d1|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, α: an angle formed by an action direction of the maximum horizontal stress with respect to a standard orientation during excavation of the well, that is, an orientation of the maximum horizontal stress acting on the ground, and $\beta_1$: an angle formed by an excavation direction of the first side-wall core with respect to the standard orientation during the excavation of the well, where $d_{min}=d1|_{\phi=0}$ when $d1|_{\phi=0}<d1|_{\phi=90}$, and $d_{min}=d1|_{\phi=90}$ when $d1|_{\phi=0}>d1|_{\phi=90}$.

In a second aspect of the in-situ stress measurement method of the present invention, the method includes:

measuring a length of a maximum diameter ($D_{max}$) at which an amount of distortion relative to a diameter of a standard circle of a measurement cross section of a cylindrical boring core is largest and a length of a minimum diameter ($D_{min}$) at which the amount of distortion relative to the diameter of the standard circle is smallest based on a shape of the measurement cross section of the boring core, wherein the boring core is acquired by hollowing ground in a well located at a predetermined depth from the earth's surface out in an excavation direction of the well, and the measurement cross section of the boring core is set in a direction orthogonal to a longitudinal direction of the boring core;

measuring a length of a diameter ($d1|_{\phi=0}$) in a vertical direction of a measurement cross section of a cylindrical first side-wall core and a length of a diameter ($d1|_{\phi=90}$) in a horizontal direction of the measurement cross section of the first side-wall core based on a shape of the measurement cross section of the first side-wall core, wherein the first side-wall core is acquired by hollowing the ground in the well located at the predetermined depth out from an inside surface of the well in a direction different from the excavation direction of the well, and the measurement cross section of the first side-wall core is set in a direction orthogonal to a longitudinal direction of the first side-wall core; and calculating a maximum horizontal stress ($S_{Hmax}$) and a minimum horizontal stress ($S_{hmin}$) among the three-dimensional stress elements by third and fourth equations, wherein the third equation represents a differential stress ($\Delta S$) between a maximum horizontal stress ($S_{Hmax}$) and a minimum horizontal stress ($S_{hmin}$) acting on the ground at the predetermined depth, $$\Delta S = S_{Hmax} - S_{hmin} = \frac{E}{1+v} \cdot \frac{D_{max} - D_{min}}{D_{min}}$$

the fourth equation represents a differential stress ($\Delta \sigma|_{\beta_1}$) between a horizontal stress ($\sigma_\theta$) and a vertical stress ($\sigma_v$) that act orthogonal to the longitudinal direction of the first side-wall core, $$\Delta \sigma|_{\beta_1, r=r_1} = \frac{1}{2}(S_{Hmax} + S_{hmin})\left(1 + \frac{R^2}{r_1^2}\right) - (S_{Hmax} - S_{hmin})\left(\frac{1}{2} - 2v\frac{R^2}{r_1^2} + \frac{3R^4}{2r_1^4}\right)\cos 2(\beta_1 - \alpha) - S_V = \frac{E}{1+v} \cdot \frac{d1'|_{\phi=90} - d1'|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, α: an angle formed by an action direction of the maximum horizontal stress with respect to a standard orientation during excavation of the well, that is, an orientation of the maximum horizontal stress acting on the ground, $\beta_1$: an angle formed by an excavation direction of the first side-wall core with respect to the standard orientation during the excavation of the well, R: a radius of the well, and $r_1$: a distance from a center of the well to the measurement cross section of the first side-wall core, where $d_{min}=d1|_{\phi=0}$ when $d1|_{\phi=0}<d1|_{\phi=90}$, and $d_{min}=d1|_{\phi=90}$ when $d1|_{\phi=0}>d1|_{\phi=90}$.

In a third aspect of the in-situ stress measurement method according to the present invention, the method includes:

measuring a length of a diameter ($d1|_{\phi=0}$) in a vertical direction of a measurement cross section of a cylindrical first side-wall core and a length of a diameter ($d1|_{\phi=90}$) in a horizontal direction of the measurement cross section of the first side-wall core based on a shape of the measurement cross section of the first side-wall core, wherein the first side-wall core is acquired by hollowing ground in a well located at a predetermined depth from the earth's surface out from an inside surface of the well in a direction different from an excavation direction of the well, and the measurement cross section is set in a direction orthogonal to a longitudinal direction of the first side-wall core; and calculating a maximum horizontal stress ($S_{Hmax}$) acting on the ground at the predetermined depth among the three-dimensional stress elements by a fifth equation which represents a differential stress ($\Delta\sigma|\beta_1$) between a horizontal stress ($\sigma_\theta$) and a vertical stress ($\sigma_v$) that act orthogonal to the longitudinal direction of the first side-wall core, $$\Delta\sigma|_{\beta_1} = \frac{1}{2}(S_{Hmax} + S_{hmin}) - \frac{1}{2}(S_{Hmax} - S_{hmin})\cos 2(\beta_1 - \alpha) - S_V = \frac{E}{1+v} \cdot \frac{d1|_{\phi=90} - d1|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, $S_{hmin}$: a minimum horizontal stress acting on the ground at the predetermined depth, α: an angle formed by an action direction of the maximum horizontal stress with respect to a standard orientation during excavation of the well, that is, an orientation of the maximum horizontal stress acting on the ground, and $\beta_1$: an angle formed by an excavation direction of the first side-wall core with respect to the standard orientation during the excavation of the well, where $d_{min} = d1|_{\phi=0}$ when $d1|_{\phi=0} < d1|_{\phi=90}$, and $d_{min} = d1|_{\phi=90}$ when $d1|_{\phi=0} > d1|_{\phi=90}$.

In a fourth aspect of the in-situ stress measurement method according to the present invention, the method includes:

measuring a length of a diameter ($d1|_{\phi=0}$) in a vertical direction of a measurement cross section of a cylindrical first side-wall core and a length of a diameter ($d1|_{\phi=90}$) in a horizontal direction of the measurement cross section of the first side-wall core based on a shape of the measurement cross section of the first side-wall core, wherein the first side-wall core is acquired by hollowing ground in a well located at a predetermined depth from the earth's surface out from an inside surface of the well in a direction different from an excavation direction of a well, and the measurement cross section is set in a direction orthogonal to a longitudinal direction of the first side-wall core; and calculating a maximum horizontal stress ($S_{Hmax}$) acting on the ground at the predetermined depth among the three-dimensional stress elements by a fifth equation which represents a differential stress ($\Delta\sigma|\beta_1$) between a horizontal stress ($\sigma_\theta$) and a vertical stress ($\sigma_v$) that act orthogonal to the longitudinal direction of the first side-wall core, $$\Delta\sigma|_{\beta_1, r=r_1} = \frac{1}{2}(S_{Hmax} + S_{hmin})\left(1 + \frac{R^2}{r_1^2}\right) - (S_{Hmax} - S_{hmin})\left(\frac{1}{2} - 2v\frac{R^2}{r_1^2} + \frac{3R^4}{2r_1^4}\right)\cos 2(\beta_1 - \alpha) - S_V = \frac{E}{1+v} \cdot \frac{d1'|_{\phi=90} - d1'|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, $S_{hmin}$: a minimum horizontal stress acting on the ground at the predetermined depth, α: an angle formed by an action direction of the maximum horizontal stress with respect to a standard orientation during excavation of the well, that is, an orientation of the maximum horizontal stress acting on the ground, $\beta_1$: an angle formed by an excavation direction of the first side-wall core with respect to the standard orientation during the excavation of the well, R: a radius of the well, and $r_1$: a distance from a center of the well to the measurement cross section of the first side-wall core, where $d_{min} = d1|_{\phi=0}$ when $d1|_{\phi=0} < d1|_{\phi=90}$, and $d_{min} = d1|_{\phi=90}$ when $d1|_{\phi=0} > d1|_{\phi=90}$.

In a fifth aspect of the in-situ stress measurement method according to the present invention, the method includes:

measuring a length of a diameter ($d2a|_{\phi=0}$) in a vertical direction of a first measurement cross section of a cylindrical second side-wall core and a length of a diameter ($d2a|_{\phi=90}$) in a horizontal direction of the first measurement cross section of the second side-wall core based on a shape of the first measurement cross section of the second side-wall core, wherein the second side-wall core is acquired by hollowing ground in a well located at a predetermined depth from the earth's surface out from an inside surface of the well in a direction different from an excavation direction of the well, and the first measurement cross section of the second side-wall core is set in a direction orthogonal to a longitudinal direction of the cylindrical second side-wall core;

measuring a length of a diameter ($d2a|_{\phi=0}$) in a vertical direction of a first measurement cross section of a cylindrical second side-wall core and a length of a diameter ($d2a|_{\phi=90}$) in the horizontal direction of the second measurement cross section of the second side-wall core, wherein the second measurement cross section of the second side-wall core is different from the first measurement cross section;

measuring a length of a diameter ($d3a|_{\phi=0}$) in the vertical direction of a third measurement cross section of a cylindrical third side-wall core and a length of a diameter ($d3a|_{\phi=90}$) in the horizontal direction of the third measurement cross section of the cylindrical third side-wall core based on a shape of the third measurement cross section of the third side-wall core, wherein the third side-wall core is acquired by hollowing the ground in the well out from the inside surface of the well in a direction different from the excavation direction of the well and an excavation direction of the second side-wall core, and the third measurement cross section is set in a direction orthogonal to the longitudinal direction of a cylindrical third side-wall core;

measuring a length of a diameter ($d3b|_{\phi=0}$) in the vertical direction of a fourth measurement cross section of the third side-wall core and a length of a diameter ($d3b|_{\phi=90}$) in the horizontal direction of the fourth measurement cross section of the third side-wall core, wherein the fourth measurement cross section of the third side-wall core is different from the third measurement cross section; and, calculating a maximum horizontal stress ($S_{Hmax}$) and a minimum horizontal stress ($S_{hmin}$) acting on the ground at the predetermined depth and an angle ($\alpha$) formed by an action direction of the maximum horizontal stress with respect to a standard orientation during excavation of the well, that is an orientation of the maximum horizontal stress acting on the ground by seventh to tenth equations, wherein the seventh equation represents a differential stress ($\Delta\sigma|_{\beta_1}$) between a horizontal stress ($\sigma_\theta$) and a vertical stress ($\sigma_v$) in the first measurement cross section of the second side-wall core, $$\Delta\sigma|_{\beta_2,r=r_{2a}} = \frac{1}{2}(S_{Hmax}+S_{hmin})\left(1+\frac{R^2}{r_{2a}^2}\right) - (S_{Hmax}-S_{hmin})\left(\frac{1}{2}-2v\frac{R^2}{r_{2a}^2}+\frac{3R^4}{2r_{2a}^4}\right)$$
$$\cos 2(\beta_2-\alpha) - S_V = \frac{E}{1+v} \cdot \frac{d2a|_{\phi=90}-d2a|_{\phi=0}}{d_{min}}$$

the eighth equation represents the differential stress ($\Delta\sigma|_{\beta_2}$) between the horizontal stress ($\sigma_\theta$) and the vertical stress ($\sigma_v$) in the second measurement cross section of the second side-wall core, $$\Delta\sigma|_{\beta_2,r=r_{2b}} = \frac{1}{2}(S_{Hmax}+S_{hmin})\left(1+\frac{R^2}{r_{2b}^2}\right) - (S_{Hmax}-S_{hmin})\left(\frac{1}{2}-2v\frac{R^2}{r_{2b}^2}+\frac{3R^4}{2r_{2b}^4}\right)$$
$$\cos 2(\beta_2-\alpha) - S_V = \frac{E}{1+v} \cdot \frac{d2b|_{\phi=90}-d2b|_{\phi=0}}{d_{min}}$$

the ninth equation represents a differential stress ($\Delta\sigma|_{\beta_2}$) between the horizontal stress ($\sigma_\theta$) and the vertical stress ($\sigma_v$) in the third measurement cross section of the third side-wall core, and $$\Delta\sigma|_{\beta_3,r=r_{3a}} = \frac{1}{2}(S_{Hmax}+S_{hmin})\left(1+\frac{R^2}{r_{3a}^2}\right) - (S_{Hmax}-S_{hmin})\left(\frac{1}{2}-2v\frac{R^2}{r_{3a}^2}+\frac{3R^4}{2r_{3a}^4}\right)$$
$$\cos 2(\beta_3-\alpha) - S_V = \frac{E}{1+v} \cdot \frac{d3a|_{\phi=90}-d3a|_{\phi=0}}{d_{min}}$$

the tenth equation represents the differential stress ($\Delta\sigma|_{\beta_3}$) between the horizontal stress ($\sigma_\theta$) and the vertical stress ($\sigma_v$) in the fourth measurement cross section of the third side-wall core, $$\Delta\sigma|_{\beta_3,r=r_{3b}} = \frac{1}{2}(S_{Hmax}+S_{hmin})\left(1+\frac{R^2}{r_{3b}^2}\right) - (S_{Hmax}-S_{hmin})\left(\frac{1}{2}-2v\frac{R^2}{r_{3b}^2}+\frac{3R^4}{2r_{3b}^4}\right)$$
$$\cos 2(\beta_3-\alpha) - S_V = \frac{E}{1+v} \cdot \frac{d3b|_{\phi=90}-d3b|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, $\beta_2$: an angle formed by an excavation direction of the second side-wall core with respect to the standard orientation during the excavation of the well, $\beta_3$: an angle formed by an excavation direction of the third side-wall core with respect to the standard orientation during the excavation of the well, R: a radius of the well, $r_{2a}$: a distance from a center of the well to the first measurement cross section of the second side-wall core, $r_{2b}$: a distance from the center of the well to the second measurement cross section of the second side-wall core, $r_{3a}$: a distance from the center of the well to the third measurement cross section of the third side-wall core, and $r_{3b}$: a distance from the center of the well to the fourth measurement cross section of the third side-wall core, where $d_{min}=d2a|_{\phi=0}$ when $d2a|_{\phi=0}<d2a|_{\phi=90}$, and $d_{min}=d2a|_{\phi=90}$ when $d2a|_{\phi=0}>d2a|_{\phi=90}$, in equation (7), $d_{min}=d2b|_{\phi=0}$ when $d2b|_{\phi=0}<d2b|_{\phi=90}$, and $d_{min}=d2b|_{\phi=90}$ when $d2a|_{\phi=0}>d2a|_{\phi=90}$, in equation (8), $d_{min}=d3a|_{\phi=0}$ when $d3a|_{\phi=0}<d3a|_{\phi=90}$, and $d_{min}=d3|_{\phi=90}$ when $d3a|_{\phi=0}<d3a|_{\phi=90}$, and in equation (9), $d_{min}=d3b|_{\phi=0}$ when $d3b|_{\phi=0}<d3b|_{\phi=90}$, and $d_{min}=d3b|_{\phi=90}$ when $d3b|_{\phi=0}>d3b|_{\phi=90}$.

In a sixth aspect of the in-situ stress measurement method according to the present invention, the method includes:

measuring a length of a diameter ($d4|_{\phi=0}$) in a vertical direction of a measurement cross section of a cylindrical fourth side-wall core and a length of a diameter ($d4|_{\phi=90}$) in a horizontal direction of the measurement cross section of the fourth side-wall core based on a shape of the measurement cross section of the fourth side-wall core, wherein the fourth side-wall core is acquired by hollowing ground in a well located at a predetermined depth from the earth's surface out from an inside surface of the well in a direction different from an excavation direction of the well, and the measurement cross section of the fourth side-wall core is set in a direction orthogonal to a longitudinal direction of a cylindrical fourth side-wall core;

measuring a length of a diameter ($d5|_{\phi=0}$) in the vertical direction a measurement cross section of a cylindrical fifth side-wall core and a length of a diameter ($d5|_{\phi=90}$) in the horizontal direction of the measurement cross section of the fifth side-wall core based on a shape of the measurement cross section of the fifth side-wall core, wherein the fifth side-wall core is acquired by hollowing the ground in the well out from the inside surface of the well in a direction different from the excavation direction of the well and an excavation direction of the fourth side-wall core, and the measurement cross section of the fifth side-wall core is set in a direction orthogonal to the longitudinal direction of a cylindrical fifth side-wall core;

measuring a length of a diameter ($d6|_{\phi=0}$) in the vertical direction of a measurement cross section of a cylindrical sixth side-wall core and a length of a diameter ($d6|_{\phi=90}$) in the horizontal direction of the measurement cross section of the sixth side-wall core based on a shape of the measurement cross section of the sixth side-wall core, wherein the sixth side-wall core is acquired by hollowing the ground in the well out from the inside surface of the well in a direction different from the excavation direction of the well and excavation directions of the fourth and fifth side-wall cores, and the measurement cross section of the sixth side-wall core is set in a direction orthogonal to the longitudinal direction of a cylindrical sixth side-wall core; and calculating a maximum horizontal stress ($S_{Hmax}$) and a minimum horizontal stress ($S_{hmin}$) acting on the ground at the predetermined depth and an angle ($\alpha$) formed by an action direction of the maximum horizontal stress with respect to a standard orientation during excavation of the well, that is an orientation of the maximum horizontal stress acting on the ground by eleventh to thirteenth equations, wherein the eleventh equation represents a differential stress ($\Delta\sigma|_{\beta 4}$) between a horizontal stress ($\sigma_\theta$) and a vertical stress ($\sigma_v$) in the measurement cross section of the fourth side-wall core, $$\Delta\sigma|_{\beta 4} = \frac{1}{2}(S_{Hmax} + S_{hmin}) - \frac{1}{2}(S_{Hmax} - S_{hmin})\cos 2(\beta_4 - \alpha) - S_V = \frac{E}{1+v} \cdot \frac{d4|_{\phi=90} - d4|_{\phi=0}}{d_{min}}$$

the twelfth equation represents the differential stress ($\Delta\sigma|_{\beta 5}$) between the horizontal stress ($\sigma_\theta$) and the vertical stress ($\sigma_v$) in the measurement cross section of the fifth side-wall core, and $$\Delta\sigma|_{\beta 5} = \frac{1}{2}(S_{Hmax} + S_{hmin}) - \frac{1}{2}(S_{Hmax} - S_{hmin})\cos 2(\beta_5 - \alpha) - S_V = \frac{E}{1+v} \cdot \frac{d5|_{\phi=90} - d5|_{\phi=0}}{d_{min}}$$

the thirteenth equation represents a differential stress ($\Delta\sigma|_{\beta 6}$) between the horizontal stress ($\sigma_\theta$) and the vertical stress ($\sigma_v$) in the measurement cross section of the sixth side-wall core, $$\Delta\sigma|_{\beta 6} = \frac{1}{2}(S_{Hmax} + S_{hmin}) - \frac{1}{2}(S_{Hmax} - S_{hmin})\cos 2(\beta_6 - \alpha) - S_V = \frac{E}{1+v} \cdot \frac{d6|_{\phi=90} - d6|_{\phi=0}}{d_{min}}$$

where degrees of variables below are regarded as being already known:
E: Young's modulus of the ground, v: Poisson's ratio of the ground,
$S_v$: a vertical stress acting on the ground at the predetermined depth,
$\beta_4$: an angle formed by an excavation direction of the fourth side-wall core with respect to the standard orientation during the excavation of the well,
$\beta_5$: an angle formed by an excavation direction of the fifth side-wall core with respect to the standard orientation during the excavation of the well, and
$\beta_6$: an angle formed by an excavation direction of the sixth side-wall core with respect to the standard orientation during the excavation of the well,
where $d_{min}=d4|_{\phi=0}$ when $d4|_{\phi=0}<d4|_{\phi=90}$, and $d_{min}=d4|_{\phi=90}$ when $d4|_{\phi=0}>d4|_{\phi=90}$,
$d_{min}=d5|_{\phi=0}$ when $d5|_{\phi=0}<d5|_{\phi=90}$, and $d_{min}=d5|_{\phi=90}$ when $d5|_{\phi=0}>d5|_{\phi=90}$, and
$d_{min}=d6|_{\phi=0}$ when $d6|_{\phi=0}<d6|_{\phi=90}$, and $d_{min}=d6|_{\phi=90}$ when $d6|_{\phi=0}>d6|_{\phi=90}$.

In the first or second aspect of the in-situ stress measurement method according to the present invention,
an angle formed by the standard orientation during the excavation of the well and a direction of the maximum diameter ($D_{max}$) in the measurement cross section of the boring core may be regarded as the angle ($\alpha$) formed by the action direction of the maximum horizontal stress with respect to the standard orientation.

Advantageous Effects of Invention

According to each of the aspects of the present invention, it is possible to precisely evaluate the dynamic environment around the tectonic ground by accurately measuring three-direction stresses, and thus, in petroleum gas wells intended for the continuous production of underground fossil fuels, it is possible to effectively carry out fracturing on the tectonic ground. As a result, it is possible to efficiently mine not only petroleum but also underground fossil fuels such as natural gas and the like through fractures.

Additionally, in energy development fields such as methane hydrate mining or geothermal utilization, the prediction of volcanic eruption or earthquakes, the underground storage of carbon dioxide, the geological disposal of radioactive waste, and the like, it becomes significantly important to evaluate stresses in rock grounds at a deep depth, and stresses in rock grounds can be accurately measured by excavating a pilot tunnel in the tectonic ground that is a subject of the above-described projects and carrying out the present invention.

In addition, in the first aspect and the second aspect of the present invention in which the boring core and the side-wall core of the well are used, the degrees of three-direction stresses acting on the tectonic ground at a certain depth are measured using the boring core acquired by hollowing the tectonic ground at the predetermined depth during the excavation of the well and the side-wall core acquired by hollowing the tectonic ground out at approximately the same depth as the depth at which the boring core has been acquired in a direction different from the well, and the stress state of the tectonic ground is evaluated on the basis of the degrees of the three-direction stresses. According to the present invention, a plurality of sample cores acquired at the same depth is used, and thus it is possible to increase the accuracy of the measurement of the main stress.

In the third aspect and the fourth aspect of the present invention in which a single side-wall core and stress information by a different method are combined together, the degrees of three-direction stresses acting on the tectonic ground at a predetermined depth are measured by combining the side-wall core acquired by hollowing the tectonic ground at the predetermined depth in the well in a direction different from the well and the stress information obtained by the different method, and the stress state of the tectonic ground is evaluated on the basis of the degrees of the three-direction stresses. Boring cores are acquired in fragments during the excavation of wells, and thus there is a case where there are no boring cores acquired at a depth at which main stresses need to be measured afterwards. However, side-wall cores can be acquired at any depths as necessary after the excavation of wells. Therefore, according to the present invention, it is possible to measure the degrees of the three-direction stresses at any depths regardless of the presence or absence of boring cores, and it is possible to precisely acknowledge the properties of the tectonic ground with a high accuracy throughout the entire region.

In the fifth aspect and the sixth aspect of the present invention in which a plurality of side-wall cores is used, the degrees of three-direction stresses acting on the tectonic ground at a predetermined depth are measured using a plurality of the side-wall cores acquired by hollowing the tectonic ground at the predetermined depth in the well in a direction different from the well, and the stress state of the tectonic ground is evaluated on the basis of the degrees of the three-direction stresses. Boring cores are acquired in fragments during the excavation of wells, and thus there is a case where there are no boring cores acquired at a depth at which main stresses need to be measured afterwards. However, side-wall cores can be acquired at any depths as necessary after the excavation of wells. Therefore, according to the present invention, it is possible to measure the degrees of the three-direction stresses at any depths regardless of the presence or absence of boring cores, and it is possible to precisely acknowledge the properties of the tectonic ground with a high accuracy throughout the entire region.

DESCRIPTION OF EMBODIMENTS

First Embodiment

Hereinafter, a first embodiment of an in-situ stress measurement method according to the present invention will be described in detail with reference to FIG. 1A to FIG. 6.

Figure 1A:
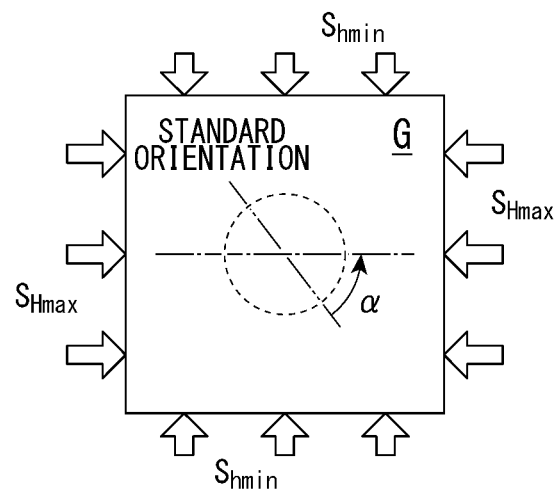
FIG. 1A is a view describing a first embodiment of an in-situ stress measurement method according to the present invention and a view schematically showing a status in which, among three-dimensional stresses acting on tectonic ground located at a predetermined depth from the earth's surface, a maximum horizontal stress ($S_{Hmax}$) and a minimum horizontal stress ($S_{hmin}$) act on the same ground.

Three-dimensional stress elements of tectonic ground include four elements of a maximum horizontal stress, a minimum horizontal stress, a vertical stress, and a direction in which the maximum horizontal stress acts, and, on the tectonic ground below the earth's surface, a variety of forces represented by the above-described three-dimensional stress elements act in any places. On a certain place in the tectonic ground which is located at a predetermined depth from the earth's surface, it is possible to regard that the maximum horizontal stress ($S_{Hmax}$) acts on the inside of a horizontal plane in the ground in a certain direction, the minimum horizontal stress ($S_{hmin}$) acts in a direction orthogonal to the direction in which the maximum horizontal stress ($S_{Hmax}$) acts, and, furthermore, a vertical stress ($S_v$) acts in the vertical direction as shown in FIG. 1A.

Figure 1B:
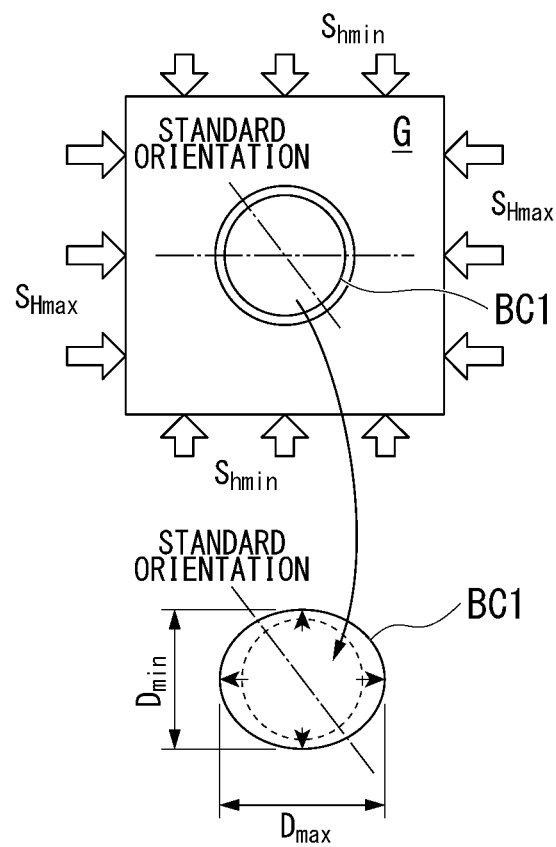
FIG. 1B is a view describing the first embodiment of the in-situ stress measurement method according to the present invention and a view schematically showing a shape in which a cross section of a boring core is acquired in a process of excavating a well from the ground located at a depth.

Let us say that a cylindrical boring core is acquired by excavating a petroleum gas well vertically downwards from the earth's surface in the tectonic ground and hollowing ground G out in an excavation direction of a well as shown in FIG. 1B at a predetermined depth. On the ground G from which the boring core needs to be acquired, the maximum horizontal stress the minimum horizontal stress ($S_{hmin}$), and the vertical stress ($S_v$) act as described above, and thus the ground G is in a state of being compressed from the circumference in a horizontal plane and, furthermore, being compressed in a boring core longitudinal direction. When the ground G in the above-described state is hollowed out in the excavation direction of the well and removed from the well as a boring core BC1, the boring core BC1 is relaxed from the stresses acting from the circumference and thus extends in the longitudinal direction and expands so as to increase the diameter. When seen in a cross section orthogonal to the longitudinal direction of the boring core BC1, that is, a cross section present in the horizontal plane in the ground, the boring core that is a precise circle in the ground is relieved from restraint and enlarges from the center so that the diameter increases in all directions around the circumference.

When a measurement cross section is set in the boring core BC1 removed from the well in a direction orthogonal to the longitudinal direction at a certain location in the longitudinal direction, and the shape of the measurement cross section is observed, the amount of expansion in a direction in which the maximum horizontal stress ($S_{Hmax}$) acts is largest, and the amount of expansion in a direction in which the minimum horizontal stress ($S_{hmin}$) acts is smallest as shown in FIG. 1B. In other words, in the direction in which the maximum horizontal stress ($S_{Hmax}$) acts, the amount of distortion relative to a diameter of a standard circle (the diameter of the boring core BC1 when receiving a horizontal stress in the ground) of the measurement cross section appears to be largest, in the direction in which the minimum horizontal stress ($S_{hmin}$) acts, the amount of distortion relative to the diameter of the standard circle of the measurement cross section appears to be smallest, and the boring core changes to an elliptical shape as a whole.

Figure 2A:
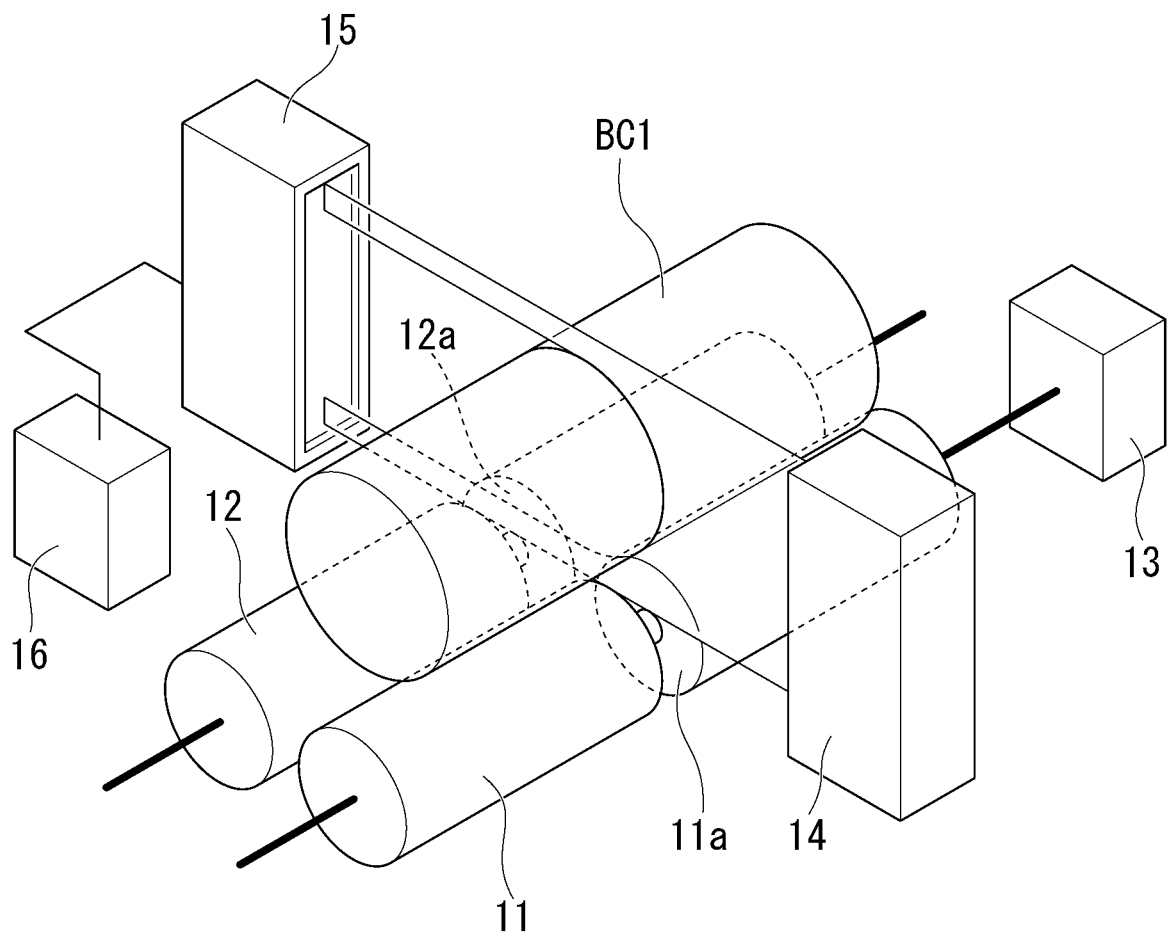
FIG. 2A is a schematic view of a measurement apparatus for measuring a diameter of the boring core and a perspective view showing a state in which the boring core is mounted in the measurement apparatus.
Figure 2B:
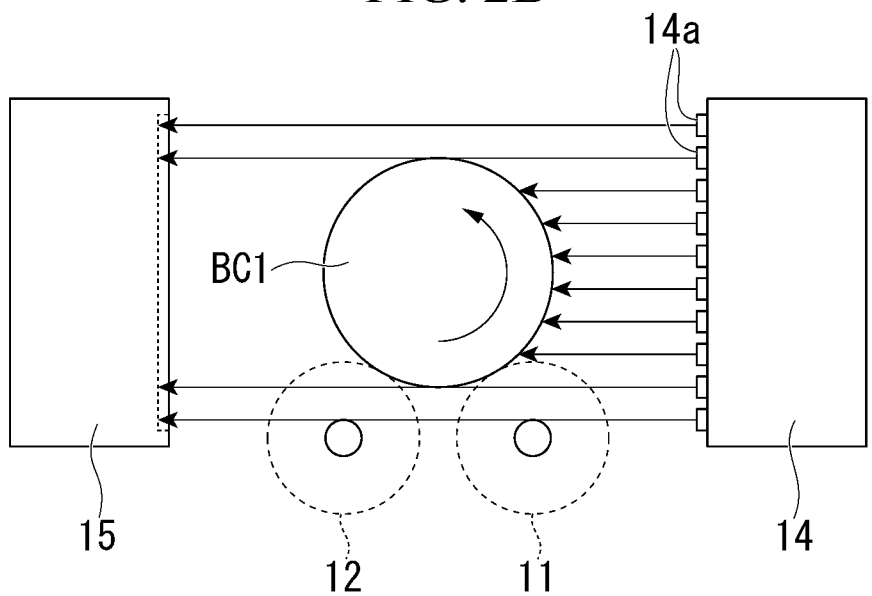
FIG. 2B is a schematic view of the measurement apparatus for measuring the diameter of the boring core and a view schematically showing a shape in which LED light radiated from a radiation portion to the boring core is received by a light-receiving portion.

Here, a diameter of a portion at which the amount of distortion relative to the diameter of the standard circle of the measurement cross section of the boring core BC1 appears to be largest is regarded as a maximum diameter ($D_{max}$), a diameter of a portion at which the amount of distortion relative to the diameter of the standard circle of the measurement cross section appears to be smallest is regarded as a minimum diameter $D_{min}$), and lengths thereof are measured. As shown in FIG. 2A, the boring core BC1 is mounted in a measurement apparatus as a specimen. The measurement apparatus is provided with a pair of rollers 11 and 12 that are arranged in parallel and are rotatable. The first roller 11 is rotated by a driving device 13. Contracted portions 11a and 12a are formed at almost the centers of both rollers 11 and 12 in the longitudinal direction. The boring core BC1 as the specimen is placed on both rollers 11 and 12 astride and is rotated reversely with respect to both rollers by rotating both rollers in the same direction. A radiation portion 14 that is configured to radiate LED light toward almost the centers of both rollers 11 and 12 is provided on one side of both rollers 11 and 12. In the radiation portion 14, a plurality of LED elements 14a that emit highly directional LED light is disposed in tandem. LED light radiated from the radiation portion 14 is radiated as if the LED light traverses the boring core BC1 placed on both rollers 11 and 12 in a cross-sectional direction thereof as shown in FIG. 2B. LED light is radiated through the contracted portions 11a and 12a of both rollers 11 and 12 and is thus not blocked by either roller. On the other side of both rollers 11 and 12, a light-receiving portion 15 that is configured to receive LED light radiated from the radiation portion 14 is provided. The width of LED light radiated from the radiation portion 14 is wider than the diameter of the boring core BC1, the light-receiving portion 15 receives LED light that is not blocked by the boring core BC1 in a vertically split form. A measuring instrument 16 that is configured to measure the diameter of the boring core BC1 is connected to the light-receiving portion 15.

The measurement apparatus configured as described above rotates the boring core BC1 at a constant rate using the driving device 13 and radiates LED light toward the boring core BC1 from the light receiver 15. LED light radiated to the boring core BC1 is partially blocked by the core, but is vertically split and received by the light-receiving portion 15. The measuring instrument 16 specifies an interval of the LED light received by the light-receiving portion 15 in a vertically split form and measures the diameter of the boring core BC1. That is, the boring core BC1 is rotated once while radiating LED light to the boring core BC1, and the diameter of the boring core BC1 is paired and recorded with every rotation angle, whereby the diameter of the boring core BC1 can be measured throughout the entire circumference of the core. This measurement apparatus can also be used to observe the cross-sectional shape of a side-wall core.

Figure 3:
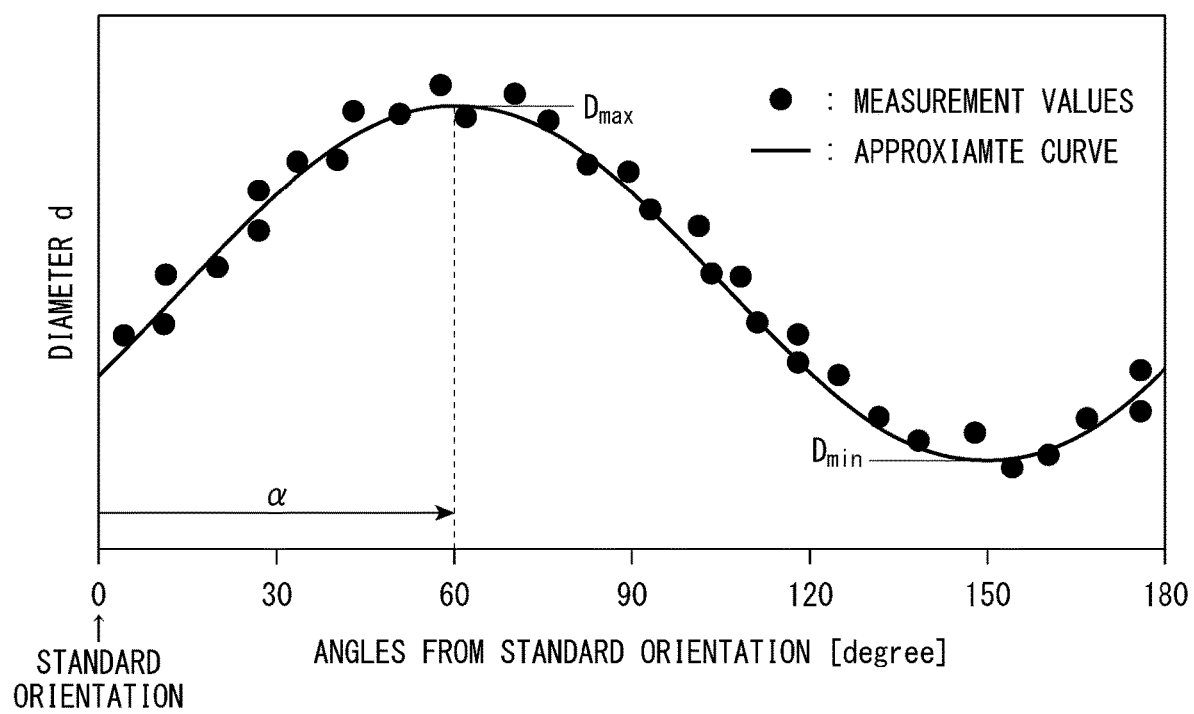
FIG. 3 is a graph showing results of measuring a length of a cross-sectional diameter of the boring core throughout the entire circumference of the core.

When plotted, the measurement results of the cross-sectional shape of the boring core BC1 by the measurement apparatus can be shown in a graph of FIG. 3. This graph shows the diameter of the boring core BC1 that changes along angles from a standard orientation from, as a starting point, one point of the outer circumference at which the standard orientation intersects with the circumference. The plotted points include errors, and thus an approximate curve is obtained using the least-square method or the like (a sine curve in the graph). The maximum value appearing on this approximate curve is the length of the maximum diameter ($D_{max}$) of the measurement cross section, and it is possible to regard that the maximum horizontal stress ($S_{Hmax}$) acts in that direction. In addition, the minimum value appearing on this approximate curve is the length of the minimum diameter ($D_{min}$) of the measurement cross section, and it is possible to regard that the minimum horizontal stress ($S_{Hmin}$) acts in that direction.

A portion in the ground toward which the boring core BC1 faces as the standard orientation, that is, the standard orientation of the boring core BC1 can be found using, for example, a method as described below. That is, image data of an inner circumferential surface of the well captured throughout the entire circumference at the depth at which the boring core BC1 has been acquired are acquired. At this time, in the image data of the inner circumferential surface, a characteristic that shows where the standard orientation faces (the inclination, conglomerate, and the like of a stripe pattern) appears, and thus, when the image data of the inner circumferential surface of the well and the state of the outer circumference of the boring core BC1 are compared with each other, which direction in the ground the boring core BC1 faces as the standard orientation is clarified. Alternatively, a function capable of recording a direction in the ground that the boring core BC1 faces as the standard orientation may be added to an excavation apparatus that is configured to be inserted into the well to acquire the boring core BC1.

Figure 4:
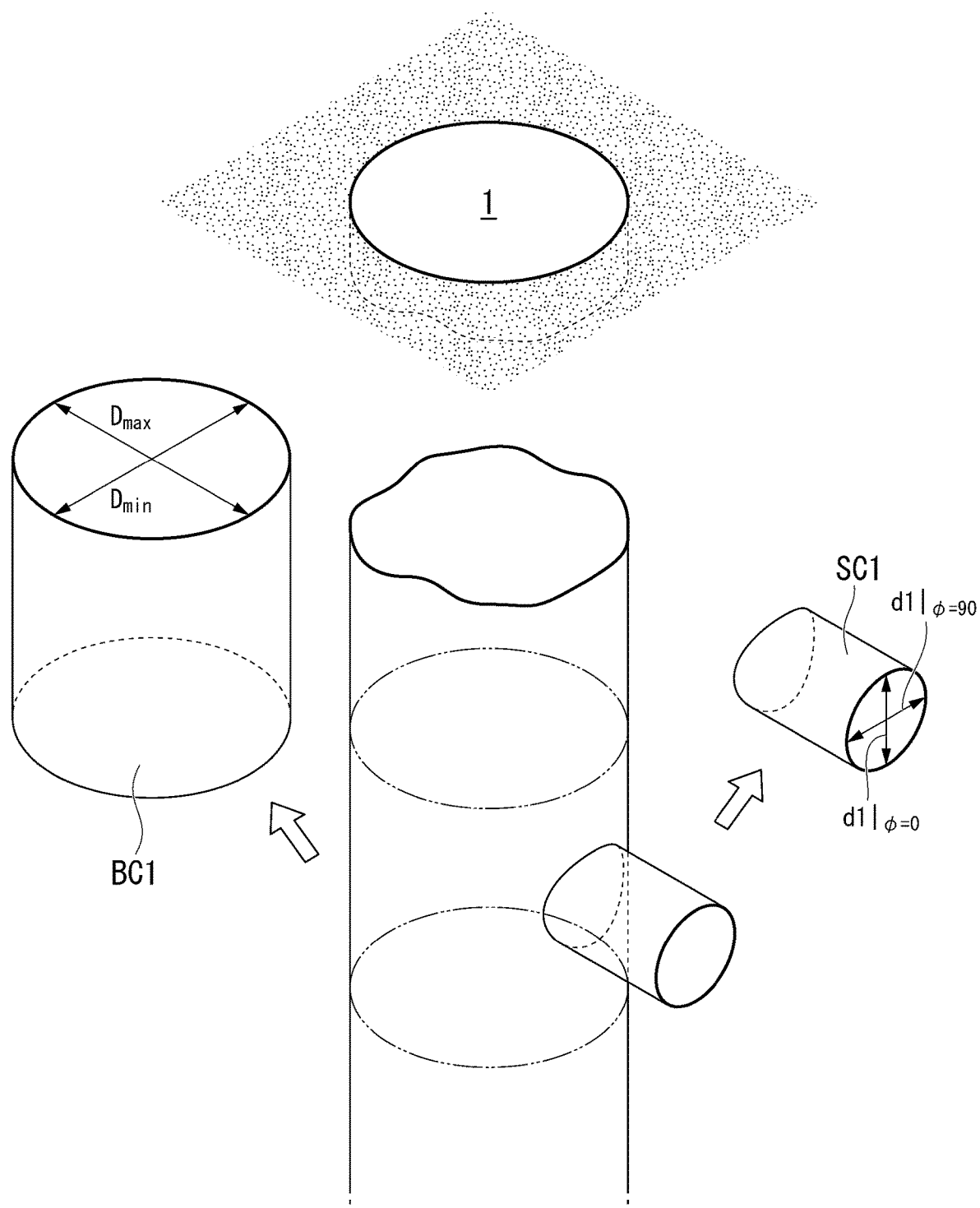
FIG. 4 is a view schematically showing a shape in which the boring core and a side-wall core are acquired from the tectonic ground located at the predetermined depth from the earth's surface.
Figure 5:
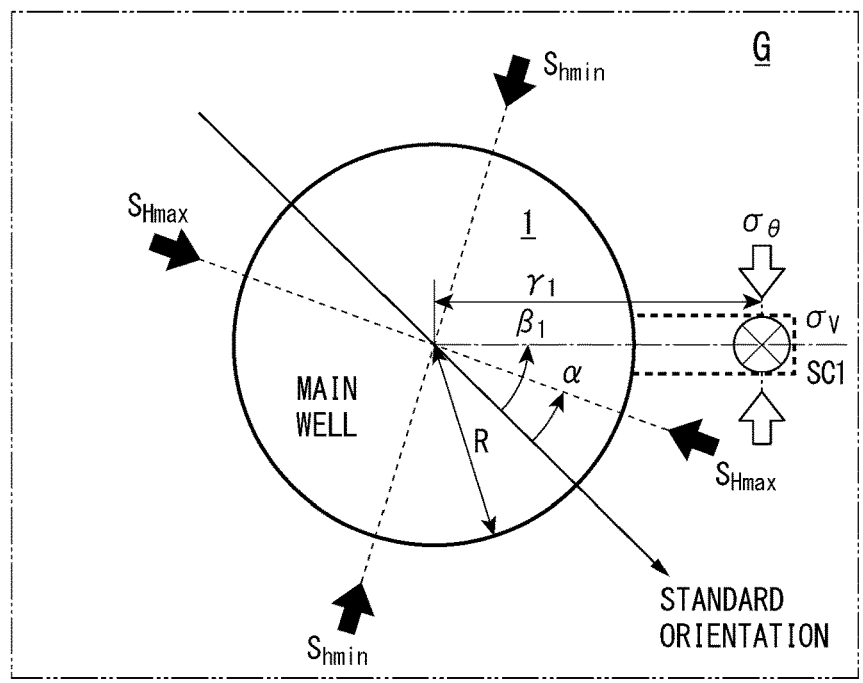
FIG. 5 is a view schematically showing a status in which, among three-dimensional stresses, a maximum horizontal stress ($S_{Hmax}$) and a minimum horizontal stress ($S_{hmin}$) act on the tectonic ground located at the predetermined depth from the earth's surface and showing a location of the side-wall core that is to be acquired from the well.
Figure 6:
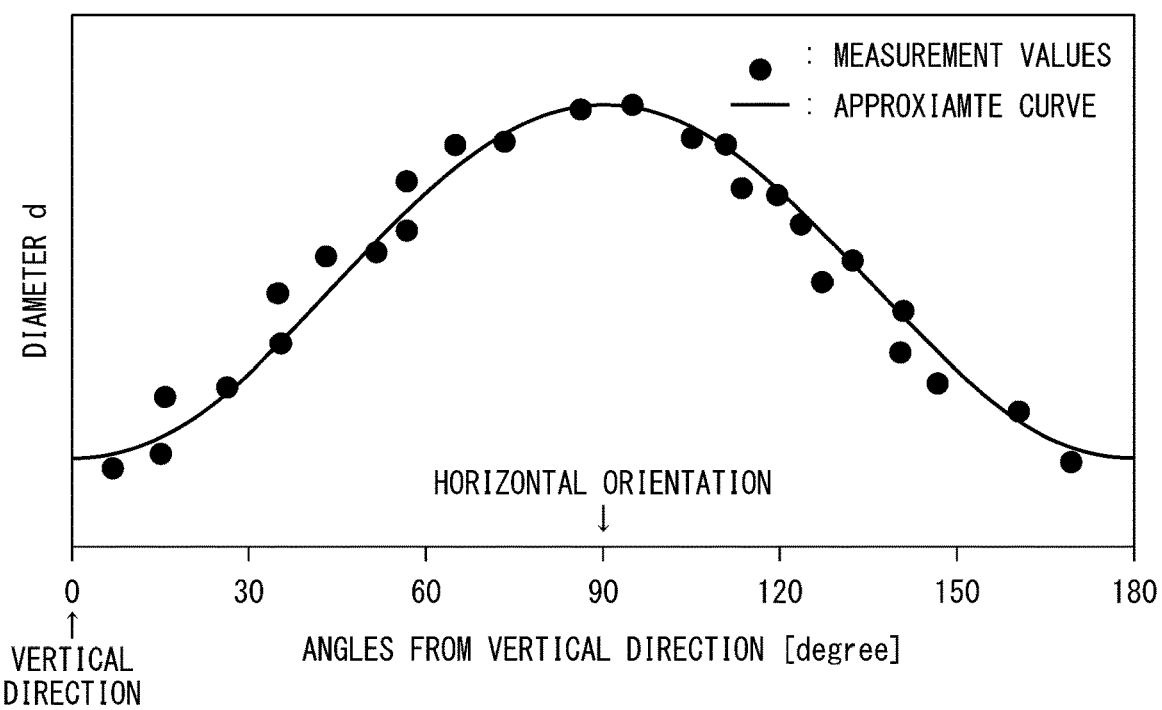
FIG. 6 is a graph showing results of measuring a length of a cross-sectional diameter of the side-wall core throughout the entire circumference of the core.

Next, as shown in FIG. 4, a cylindrical side-wall core SC1 is acquired by hollowing the tectonic ground from which a petroleum gas well needs to be excavated out from an inside surface of a well at the same depth as the depth at which the boring core BC1 is acquired in a direction orthogonal to an excavation direction of the well, that is, a certain direction in a horizontal plane. On the ground G from which the side-wall core SC1 needs to be acquired, a maximum horizontal stress ($S_{Hmax}$), a minimum horizontal stress ($S_{hmin}$), and a vertical stress ($S_v$), which are the same as those in FIG. 1A, act as shown in FIG. 5, and thus, when the ground G is hollowed out from the inside surface of the well at the same depth as the depth at which the boring core BC1 is acquired in a certain direction in the horizontal plane and removed from the well as the side-wall core SC1, the side-wall core SC1 is relaxed from the stresses acting from the circumference and thus, similar to the boring core BC1, extends in the longitudinal direction and expands so as to increase the diameter. When seen in a cross section orthogonal to the longitudinal direction of the side-wall core SC1, that is, a cross section present in a vertical plane in the ground, the side-wall core that is a precise circle in the ground is relieved from restraint and enlarges from the center so that the diameter increases in all directions around the circumference.

A measurement cross section is set in the side-wall core SC1 removed from the well in a direction orthogonal to the longitudinal direction at a certain location in the longitudinal direction. This measurement cross section is specified by a distance by which the side-wall core SC1 is away from the central axis of the well (main well) in the radial direction of the well when present in the ground. Here, a distance from the center of the well to the measurement cross section of the side-wall core SC1 is represented by ($r_1$), and the measurement cross section is specified by the size thereof. In addition, when the shape of the measurement cross section is observed, the side-wall core SC1 is relaxed from both a vertical stress ($\sigma_v$) acting in the vertical direction and a horizontal stress ($\sigma_\theta$) acting in the horizontal direction when the side-wall core is present in the ground and thus changes in an elliptical shape in which the major diameter or the minor diameter accordingly lies in a direction in which the vertical stress ($\sigma_v$) acts. In detail, at the predetermined depth at which the side-wall core SC1 is acquired, when the vertical stress ($S_v$) is clearly larger than the maximum horizontal stress ($S_{Hmax}$) and the minimum horizontal stress ($S_{hmin}$), the measurement cross section of the side-wall core SC1 changes so that a diameter ($d1|_{\phi=0}$) in a direction in which the vertical stress ($\sigma_v$) acts when the side-wall core SC1 is present in the ground becomes longer than a diameter ($d1|_{\phi=90}$) in a direction in which the horizontal stress ($\sigma_\theta$) acts when, similarly, the side-wall core SC1 is present in the ground, and, when the vertical stress ($S_v$) is clearly smaller than the maximum horizontal stress ($S_{Hmax}$) and the minimum horizontal stress ($S_{hmin}$), the measurement cross section of the side-wall core SC1 changes so that the diameter ($d1|_{\phi=0}$) in the direction in which the vertical stress ($\sigma_v$) acts becomes shorter than the diameter ($d1|_{\phi=90}$) in the direction in which the horizontal stress ($\sigma_\theta$) acts when, similarly, the side-wall core SC1 is present in the ground.

Here, the length of the diameter of the side-wall core SC1 which lies in the vertical direction when the side-wall core is present in the ground, that is, the diameter ($d1|_{\phi=0}$) of the measurement cross section in the vertical direction and the length of the diameter which lies in the horizontal direction when the side-wall core is present in the ground, that is, the diameter ($d1|_{\phi=90}$) of the measurement cross section in the horizontal direction are measured. Similar to the case of the boring core, the side-wall core SC1 is installed in the measurement apparatus as a specimen, and the diameter of the side-wall core SC1 is measured throughout the circumference (360°) of the core. When plotted, the measurement results can be shown in a graph of FIG. 6. This graph shows, with a direction that lies in the vertical direction when the side-wall core SC1 is present in the ground regarded as a standard direction, the diameter of the side-wall core SC1 that changes along angles from the standard direction from, as a starting point, one point of the outer circumference at which the standard direction intersects with the circumference. The plotted points include errors, and thus an approximate curve is obtained using the least-square method or the like (a sine curve in the graph). On this approximate curve, at the predetermined depth at which the side-wall core SC1 is acquired, when the vertical stress ($S_v$) is larger than the maximum horizontal stress ($S_{Hmax}$) and the minimum horizontal stress ($S_{hmin}$), the maximum value appears at points at which the angle from the standard direction is 0° and 180°, and, thus, in the measurement cross section of the side-wall core SC1, the diameter ($d1|_{\phi=0}$) in the vertical direction becomes longer than the diameter ($d1|_{\phi=90}$) in the horizontal direction. In addition, when the vertical stress ($S_v$) is smaller than the maximum horizontal stress ($S_{Hmax}$) and the minimum horizontal stress $S_{hmin}$), the maximum value appears at a point at which the angle from the standard direction is 90°, and thus, in the measurement cross section of the side-wall core SC1, the diameter ($d1|_{\phi=0}$) in the vertical direction becomes shorter than the diameter ($d1|_{\phi=90}$) in the horizontal direction.

An excavation direction of the side-wall core SC1 can be specified using, for example, a method as described below as an angle ($\beta_1$) formed by the excavation direction of the side-wall core SC1 with respect to a standard orientation during the excavation of the well. That is, after the acquisition of the side-wall core SC1, image data of an inner circumferential surface of the well captured throughout the entire circumference at the depth at which the side-wall core has been acquired are acquired. At this time, in the image data of the inner circumferential surface of the well, a hole after the excavation of the side-wall core SC1 appears, and thus the degree of the angle ($\beta_1$) formed by the excavation direction of the side-wall core SC1 with respect to the standard orientation is clarified by how far the hole is away from the standard orientation. Alternatively, image data of the inner circumferential surface of the well captured before the acquisition of the side-wall core SC1 and an image of a cross section of the side-wall core SC1 are compared with each other, and, if a portion that coincides with the cross-sectional image of the side-wall core SC1 is present in the image data of the inner circumferential surface of the well, it is found that the side-wall core SC1 has been excavated from that portion, and thus the degree of the angle ($\beta_1$) formed by the excavation direction of the side-wall core SC1 with respect to the standard orientation is clarified by haw far the portion is away from the standard orientation. Additionally, a function capable of freely setting or measuring the excavation direction of the side-wall core SC1 with respect to the standard orientation of the well may be added to an excavation apparatus that is configured to be inserted into the well to acquire the side-wall core SC1.

Hereinafter, on the basis of information obtained by observing the boring core BC1 and the side-wall core SC1 acquired from the tectonic ground present at a predetermined depth from the earth's surface, three-dimensional stress elements acting on the tectonic ground from which the two cores are acquired will be obtained.

First, the fact that the degree of the vertical stress ($S_v$) can be obtained using an equation below as an overburden pressure is known in the related art.

$$S_v = \rho g h$$

($\rho$: an average density of a geological layer in a region from the earth's surface to a point at a depth h, g: acceleration of gravity, h: a depth from the earth's surface)

The degree of information ($\rho$, g, and h) necessary to obtain the vertical stress ($S_v$) is not dependent on the information obtained by observing the two cores but is already known. For example, $\rho$ can be found by density logging.

Next, a direction in which the maximum horizontal stress ($S_{Hmax}$) acts can be specified by the degree of an angle formed by the direction with respect to the standard orientation. The standard orientation can be easily understood if, for example, the direction of the north is considered as the standard orientation.

From the graph of FIG. 3, it is possible to clarify the direction of the maximum horizontal stress ($S_{Hmax}$) acting on the tectonic ground from which the boring core BC1 has been acquired. This graph shows a change in the diameter of the boring core BC1 that changes along the angles from a starting point with one point of the outer circumference at which the standard orientation intersects with the circumference set as the starting point (standard orientation 0°), and thus it is possible to regard an angle at which the maximum value appears on the approximate curve as an angle ($\alpha$) formed by the direction in which the maximum horizontal stress ($S_{Hmax}$) acts with respect to the standard orientation.

Additionally, the orientation of the maximum horizontal stress can be found by analyzing borehole breakout or drilling-induced tensile fracture caused by the excavation of the main well or evaluating the anisotropy of the S-wave velocity in a rock ground by dipole sonic waveform logging.

A differential stress (ΔS) between the maximum horizontal stress ($S_{Hmax}$) and the minimum horizontal stress ($S_{hmin}$) acting on the ground at the predetermined depth can be represented by equation (1) below $$\Delta S = S_{Hmax} - S_{hmin} = \frac{E}{1+v} \cdot \frac{D_{max} - D_{min}}{D_{min}} \quad (1)$$

In addition, a differential stress ($\Delta\sigma|\beta_2$) between the stress acting in the horizontal direction when the side-wall core SC1 is present in the ground, that is, the horizontal stress ($\sigma_\theta$) and the stress acting in the vertical direction when the side-wall core SC1 is present in the ground, that is, the vertical stress ($\sigma_v$) can be represented by equation (2) below.

$$\Delta\sigma|_{\beta_1} = \frac{1}{2}(S_{Hmax} + S_{hmin}) - \frac{1}{2}(S_{Hmax} - S_{hmin})\cos2(\beta_1 - \alpha) - S_V = \quad (2)$$
$$\frac{E}{1+v} \cdot \frac{d1|_{\phi=90} - d1|_{\phi=0}}{d_{min}}$$

In the information included in the equations (1) and (2), the degree of Young's modulus (E) of the ground and the degree of Poisson's ratio (v) of the ground are, similar to the information (ρ, g, and h) necessary to obtain the vertical stress ($S_v$), not dependent on the information obtained by observing the two cores but are already known.

The length of the maximum diameter ($D_{max}$) and the length of the minimum diameter ($D_{min}$) in the measurement cross section of the boring core BC1 which is included in equation (1) can be read from the graph of FIG. 3 obtained by plotting the observation results of the boring core BC1.

The angle ($\beta_1$) formed by the excavation direction of the side-wall core SC1 with respect to the standard orientation during the excavation of the well which is included in equation (2) can be found using the above-described method. The length of the diameter ($d1|_{\phi=0}$) in the vertical direction and the length of the diameter ($d1|_{\phi=90}$) in the horizontal direction in the measurement cross section of the side-wall core SC1 can be read from the graph of FIG. 6 obtained by plotting the observation results of the side-wall core SC1. In equation (2), when the diameter ($d1|_{\phi=0}$) in the vertical direction is shorter than the diameter ($d1|_{\phi=90}$) in the horizontal direction, the length of a minimum diameter ($d_{min}$) of the side-wall core SC1 is regarded as the length of the diameter ($d1|_{\phi=90}$) in the vertical direction, and, when the diameter ($d1|_{\phi=0}$) in the vertical direction is longer than the diameter ($d1|_{\phi=90}$) in the horizontal direction, the length of the minimum diameter ($d_{min}$) of the side-wall core SC1 is regarded as the length of the diameter ($d1|_{\phi=90}$) in the horizontal direction.

Among the three-dimensional stress elements, the remaining maximum horizontal stress ($S_{Hmax}$) and the remaining minimum horizontal stress ($S_{hmin}$) can be obtained as equations (3) below using the equations (1) and (2).

$$S_{Hmax} = \frac{1}{2}(S + \Delta S), \ S_{hmin} = \frac{1}{2}(S - \Delta S) \quad (3)$$
Here,
$$S = S_{Hmax} + S_{hmin} = 2\Delta\sigma|_{\beta_1} + \Delta S\cos2(\beta_1 - \alpha) + 2S_V$$

According to the first embodiment of the in-situ stress measurement method of the present invention, as described above, the degrees of the three-direction stresses acting on the tectonic ground at a predetermined depth in the ground are measured, and the stress state of the tectonic ground is evaluated on the basis of the degrees of the three-dimension stresses, and, particularly, according to the present embodiment, the boring core and the side-wall core acquired at the same depth are used, and thus it is possible to increase the accuracy of main stress measurement compared with those of methods of the related art.

In addition, if the three-direction stresses can be accurately measured using the present invention, a dynamic environment around the tectonic ground can be precisely evaluated, and thus, in petroleum gas wells intended for the continuous production of underground fossil fuels, it is possible to effectively carry out fracturing on the tectonic ground. As a result, it is possible to efficiently extract not only petroleum but also underground fossil fuels such as natural gas through fractures.

Additionally, in energy development fields such as methane hydrate mining or geothermal utilization, the prediction of volcanic eruption or earthquakes, the underground storage of carbon dioxide, the geological disposal of radioactive waste, and the like, it becomes significantly important to acknowledge stresses in rock grounds at a deep depth, and stresses in rock grounds can be accurately measured by excavating a pilot tunnel in the tectonic ground that is a subject of the above-described projects and carrying out the present invention.

It is needless to say that, in grounds in which a well is excavated, stress concentration occurs. It is preferable that the measurement cross section of the side-wall core SC1 can be ensured in a portion that is sufficiently far from the center of the well (main well) and is not significantly affected by stress concentration, but the length of the side-wall core SC1 is dependent on the inner diameter (radius: R) of the well (when the side-wall core SC1 is longer than the diameter (2R) of the well, it is not possible to remove the side-wall core SC1 from the well). Therefore, there are many cases where the influence of stress concentration cannot be ignored. In such a case, the differential stress ($\Delta\sigma|\beta_1$) between the horizontal stress ($\sigma_\theta$) and the vertical stress ($\sigma_v$) acting when the side-wall core SC1 is present in the ground can be represented by equation (2') below. In this case as well, the length of the diameter ($d1|_{\phi=0}$) in the vertical direction and the length of the diameter ($d1|_{\phi=90}$) in the horizontal direction in the measurement cross section of the side-wall core SC1 can be read from the graph of FIG. 6 obtained by plotting the observation results of the side-wall core SC1.

$$\Delta\sigma|_{\beta_1,r=r_1} = \quad (2')$$
$$\frac{1}{2}(S_{Hmax} + S_{hmin})\left(1 + \frac{R^2}{r_1^2}\right) - (S_{Hmax} - S_{hmin})\left(\frac{1}{2} - 2v\frac{R^2}{r_1^2} + \frac{3R^4}{2r_1^4}\right)$$
$$\cos2(\beta_1 - \alpha) - S_V = \frac{E}{1+v} \cdot \frac{d1'|_{\phi=90} - d1'|_{\phi=0}}{d_{min}}$$

Among the three-dimensional stress elements, the degrees of the remaining maximum horizontal stress ($S_{Hmax}$) and the remaining minimum horizontal stress ($S_{hmin}$) can be obtained as equations (4) below using the equations (1) and (2'). In equation (2'), when a diameter ($d1'|_{\phi=0}$) in the vertical direction is shorter than a diameter ($d1'|_{\phi=90}$) in the horizontal direction, the length of the minimum diameter ($d_{min}$) of the side-wall core SC1 is regarded as the length of the diameter ($d1'|_{\phi=0}$) in the vertical direction, and, when the diameter ($d1'|_{\phi=0}$) in the vertical direction is longer than the diameter ($d1'|_{\phi=90}$) in the horizontal direction, the length of the minimum diameter ($d_{min}$) of the side-wall core SC1 is regarded as the length of the diameter ($d1'|_{\phi=90}$) in the horizontal direction.

$$S_{Hmax} = \frac{1}{2}(S + \Delta S), S_{hmin} = \frac{1}{2}(S - \Delta S) \quad (4)$$

Here, $$S = S_{Hmax} + S_{hmin} = \frac{\Delta\sigma|_{\beta_1, r=r_1} + \Delta S\left(\frac{1}{2} - 2v\frac{R^2}{r_1^2} + \frac{3R^4}{2r_1^4}\right)}{\cos 2(\beta_1 - \alpha) + S_V}$$

$$\left(1 + \frac{R^2}{r_1^2}\right)$$

According to the first embodiment of the in-situ stress measurement method of the present invention, even in a case where the influence of stress concentration acting on the tectonic ground cannot be ignored, it is possible to increase the accuracy of main stress measurement compared with those of methods of the related art. Therefore, it becomes possible to efficiently mine underground fossil fuels such as petroleum and natural gas, and, furthermore, in a variety of projects for which the evaluation of stresses in rock grounds at a deep depth is significantly important, it becomes possible to accurately measure stresses in rock grounds by carrying out the present invention.

Second Embodiment

Next, a second embodiment of the in-situ stress measurement method according to the present invention will be described in detail. In some cases, matters that have been described in detail in the first embodiment will be only simply described in the present embodiment.

In the present embodiment, the boring core BC1 is not used, and, on the basis of information obtained by observing one side-wall core SC1 acquired from the tectonic ground present at a predetermined depth from the earth's surface, three-dimensional stress elements acting on the tectonic ground from which the same core has been acquired are obtained.

First, the degree of the vertical stress ($S_v$) can be obtained as an overburden pressure using the method of the first embodiment. Next, in the first embodiment, the direction in which the maximum horizontal stress ($S_{Hmax}$) acts is specified by acquiring the boring core BC1 and analyzing the shape thereof; however, in the present embodiment, the boring core BC1 is not used, and thus the direction in which the maximum horizontal stress ($S_{Hmax}$) acts, that is, the angle ($\alpha$) formed by the direction in which the maximum horizontal stress ($S_{Hmax}$) acts with respect to the standard orientation is specified using other methods in which cores are not required such as borehole breakout or drilling-induced tensile fracture caused by the excavation of the main well, dipole sonic waveform logging, or the like.

In addition, aside from the above-described step, the degree of the minimum horizontal stress ($S_{hmin}$) acting on the ground is obtained using the hydraulic fracturing method. The hydraulic fracturing method refers to a method in which an extremely high hydraulic pressure is exerted on the inside surface of a well to generate fractures in the ground around the well including the inside surface and the degree of the minimum horizontal stress acting on the ground through the fractures is obtained (described in detail in, for example, "Rock Stress And Its Measurement" April, 2014 by Bernard Amadei and Ove Stephansson). Additionally, the degree of the minimum horizontal stress can also be obtained by, for example, a leak off test or a formation integrity test.

The differential stress ($\Delta\sigma|_{\beta_2}$) between the stress acting in the horizontal direction when the side-wall core SC1 is present in the ground, that is, the horizontal stress ($\sigma_\theta$) and the stress acting in the vertical direction when the side-wall core SC1 is present in the ground, that is, the vertical stress ($\sigma_v$) can be represented by equation (2) that is also used in the first embodiment in a case where stress concentration is not taken into account.

$$\Delta\sigma|_{\beta_1} = \frac{1}{2}(S_{Hmax} + S_{hmin}) - \frac{1}{2}(S_{Hmax} - S_{hmin})\cos 2(\beta_1 - \alpha) - S_V = \quad (2)$$

$$\frac{E}{1+v} \cdot \frac{d1|_{\phi=90} - d1|_{\phi=0}}{d_{min}}$$

Here, the degree of the minimum horizontal stress ($S_{hmin}$) is already known by the hydraulic fracturing method, the degree of the remaining maximum horizontal stress ($S_{Hmax}$) can be obtained using equation (5) below from equation (2).

$$S_{Hmax} = \frac{\Delta\sigma|_{\beta_1} + S_V - \left\{\frac{1}{2} + \frac{1}{2}\cos 2(\beta_1 - \alpha)\right\}S_{hmin}}{\frac{1}{2} - \frac{1}{2}\cos 2(\beta_1 - \alpha)} \quad (5)$$

In a case where stress concentration is taken into account, the differential stress ($\Delta\sigma|_{\beta_1}$) can be represented by equation (2') that is also used in the first embodiment.

$$\Delta\sigma|_{\beta_1, r=r_1} = \quad (2')$$

$$\frac{1}{2}(S_{Hmax} + S_{hmin})\left(1 + \frac{R^2}{r_1^2}\right) - (S_{Hmax} - S_{hmin})\left(\frac{1}{2} - 2v\frac{R^2}{r_1^2} + \frac{3R^4}{2r_1^4}\right)$$

$$\cos 2(\beta_1 - \alpha) - S_V = \frac{E}{1+v} \cdot \frac{d1'|_{\phi=90} - d1'|_{\phi=0}}{d_{min}}$$

In this case, the degree of the remaining maximum horizontal stress ($S_{Hmax}$) can be obtained using equation (5') below.

$$S_{Hmax} = \frac{\Delta\sigma|_{\beta_1, r=r_1} + S_V - \left\{\frac{\frac{1}{2} + \frac{R^2}{2r_1^2} +}{\left(\frac{1}{2} - 2v\frac{R^2}{r_1^2} + \frac{3R^4}{2r_1^4}\right)\cos 2(\beta_1 - \alpha)}\right\}S_{hmin}}{\frac{1}{2} + \frac{R^2}{2r_1^2} - \left(\frac{1}{2} - 2v\frac{R^2}{r_1^2} + \frac{3R^4}{2r_1^4}\right)\cos 2(\beta_1 - \alpha)} \quad (5')$$

According to the second embodiment of the in-situ stress measurement method of the present invention, it is possible to measure the degrees of the three-direction stresses acting on the tectonic ground at the predetermined depth by combining information obtained from the side-wall core and stress information obtained using a different method and evaluate the stress state of the tectonic ground on the basis of the combined information. Boring cores are acquired in fragments during the excavation of wells, and thus there is a case where there are no boring cores acquired at a depth at which main stresses need to be measured afterwards, but side-wall cores can be acquired at any depths as necessary after the excavation of wells. Therefore, according to the present embodiment, it is possible to measure the degrees of the three-direction stresses at any depths using side-wall cores alone, and it is possible to precisely acknowledge the properties of the tectonic ground with a high accuracy throughout the entire region. That is, according to the second embodiment, similar to the first embodiment, it becomes possible to efficiently mine underground fossil fuels such as petroleum and natural gas, and, furthermore, in a variety of projects for which the evaluation of stresses in rock grounds at a deep depth is significantly important, it becomes possible to accurately measure stresses in rock grounds by carrying out the present invention.

Third Embodiment

Next, a third embodiment of the in-situ stress measurement method according to the present invention will be described in detail with reference to FIG. 7. In some cases, matters that have been described in detail in the first and second embodiments will be only simply described in the present embodiment.

In the present embodiment, on the basis of information obtained by observing two side-wall cores SC2 and SC3 acquired from the tectonic ground present at a predetermined depth from the earth's surface, three-dimensional stress elements acting on the tectonic ground from which the two cores have been acquired are obtained.

Figure 7:
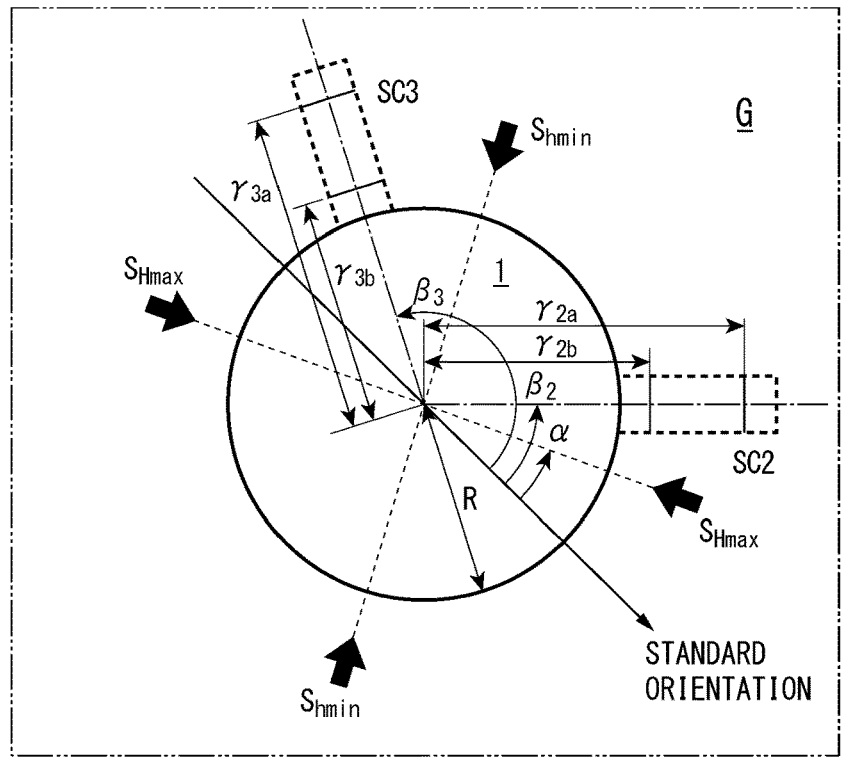
FIG. 7 is a view describing a third embodiment of the in-situ stress measurement method according to the present invention and a view schematically showing a status in which, among the three-dimensional stresses, the maximum horizontal stress ($S_{Hmax}$) and the minimum horizontal stress ($S_{hmin}$) act on the tectonic ground located at the predetermined depth from the earth's surface and showing locations of two side-wall cores that are to be acquired from the well.

First, as shown in FIG. 7, a cylindrical side-wall core (second side-wall core) SC2 is acquired by hollowing the ground out from an inside surface of a well at a predetermined depth from the earth's surface in a direction orthogonal to an excavation direction of the well, that is, a certain direction in a horizontal plane using the method in the first embodiment. It is needless to say that, on the ground from which the side-wall core SC2 has been acquired, the maximum horizontal stress ($S_{Hmax}$), the minimum horizontal stress ($S_{hmin}$), and the vertical stress ($S_v$) act, and thus, when the side-wall core SC2 is hollowed out from the ground and removed from the well, the cross-sectional shape of the side-wall core SC2 changes in the same manner as that of the side-wall core SC1.

A first measurement cross section is set in the side-wall core SC2. The first measurement cross section is specified by a distance by which the side-wall core SC2 is away from the central axis of the well (main well) in the radial direction of the well when present in the ground. Here, a distance from the center of the well to the first measurement cross section of the side-wall core SC2 is represented by ($r_{2a}$), and the location of the first measurement surface is specified by the size thereof.

Next, the length of the diameter of the side-wall core SC2 which lies in the vertical direction when the side-wall core is present in the ground, that is, a diameter ($d2a|_{\phi=0}$) of the first measurement cross section in the vertical direction and the length of the diameter which lies in the horizontal direction when the side-wall core is present in the ground, that is, a diameter ($d2a|_{\phi=90}$) of the first measurement cross section in the horizontal direction are measured using the measurement apparatus described in the first embodiment. The measurement results can be shown in the graph of FIG. 6. This graph shows, with a direction that lies in the vertical direction when the side-wall core SC2 is present in the ground regarded as a standard, the diameter of the side-wall core SC2 that changes along angles from a standard direction from, as a starting point, one point of the outer circumference at which the standard direction intersects with the circumference. The plotted points include errors, and thus an approximate curve is obtained using the least-square method or the like (a sine curve in the graph). On this approximate curve, at the predetermined depth at which the side-wall core SC2 is acquired, when the vertical stress ($S_v$) is clearly larger than the maximum horizontal stress ($S_{Hmax}$) and the minimum horizontal stress ($S_{hmin}$), the maximum value appears at points at which the angle from the standard direction is 0° and 180°, and thus, in the first measurement cross section of the side-wall core SC2, the diameter ($d2a|_{\phi=0}$) in the vertical direction becomes longer than the diameter ($d2a|_{\phi=90}$) in the horizontal direction. In addition, when the vertical stress ($S_v$) is clearly smaller than the maximum horizontal stress ($S_{Hmax}$) and the minimum horizontal stress ($S_{hmin}$), the maximum value appears at a point at which the angle from the standard direction is 90°, and thus, in the first measurement cross section of the side-wall core SC2, the diameter ($d2a|_{\phi=0}$) in the vertical direction becomes shorter than the diameter ($d2a|_{\phi=90}$) in the horizontal direction.

Next, in the side-wall core SC2, a second measurement cross section is set at a location farther than the first measurement cross section from the center of the well, a distance from the center of the well to the second measurement cross section is represented by ($r_{2b}$), and the location of the second measurement surface is specified by the size thereof.

Next, similar to the above description, the length of a diameter ($d2b|_{\phi=0}$) of the second measurement cross section in the vertical direction and the length of a diameter ($d2b|_{\phi=90}$) of the second measurement cross section in the horizontal direction are measured. The measurement results are plotted in a graph, and an approximate curve is obtained using the least-square method or the like. On this approximate curve, at the predetermined depth at which the side-wall core SC2 is acquired, when the vertical stress ($S_v$) is clearly larger than the maximum horizontal stress ($S_{Hmax}$) and the minimum horizontal stress ($S_{hmin}$), the maximum value appears at points at which the angle from the standard direction is 0° and 180°, and thus, in the second measurement cross section of the side-wall core SC2, the diameter ($d2b|_{\phi=0}$). In the vertical direction becomes longer than the diameter ($d2b|_{\phi=90}$) in the horizontal direction. In addition, when the vertical stress ($S_v$) is clearly smaller than the maximum horizontal stress ($S_{Hmax}$) and the minimum horizontal stress ($S_{hmin}$), the maximum value appears at a point at which the angle from the standard direction is 90°, and thus, in the second measurement cross section of the side-wall core SC2, the diameter ($d2b|_{\phi=0}$) in the vertical direction becomes shorter than the diameter ($d2b|_{\phi=90}$) in the horizontal direction.

Next, a cylindrical side-wall core (third side-wall core) SC3 is acquired by hollowing the ground out from an inside surface of a well at a predetermined depth from the earth's surface that is the same as the depth at which the side-wall core SC2 is acquired in a direction orthogonal to an excavation direction of the well, that is, a certain direction in a horizontal plane and a direction different from the evacuation direction of the side-wall core SC2. The cross-sectional shape of the side-wall core SC3 also changes in the same manner as that of the side-wall core SC2.

Next, a third measurement cross section is set in the side-wall core SC3, a distance from the center of the well to the third measurement cross section is represented by ($r_{3a}$), and the location of the third measurement surface is specified by the size thereof. In addition, similar to the above description, the length of a diameter ($d3a|_{\phi=0}$) of the third measurement cross section in the vertical direction and the length of a diameter ($d3a|_{\phi=90}$) of the third measurement cross section in the horizontal direction are measured. When the measurement results are plotted in a graph, and an approximate curve is obtained using the least-square method or the like, the characteristics of the maximum value and the minimum value appear in the same manner as in the side-wall core SC2.

Next, in the side-wall core SC3, the location of a fourth measurement cross section is set at a location farther than the third measurement cross section from the center of the well, and a distance from the center of the well to the fourth measurement cross section is represented by ($r_{3b}$), and the fourth measurement surface is specified by the size thereof. In addition, the length of a diameter ($d3b|_{\phi=0}$) of the fourth measurement cross section in the vertical direction and the length of a diameter ($d3b|_{\phi=90}$) in the horizontal direction are measured using the same method as described above. When the measurement results are plotted in a graph, and an approximate curve is obtained using the least-square method or the like, the characteristics of the maximum value and the minimum value appear in the same manner as in the side-wall core SC2 as expected.

The excavation directions of the side-wall cores SC2 and SC3 can be specified by setting an angle formed by the excavation direction of the side-wall core SC2 with respect to the standard orientation of the well to ($\beta_2$) and, furthermore, setting an angle formed by the excavation direction of the side-wall core SC3 with respect to the standard orientation of the well to ($\beta_3$) using the method described in the first embodiment.

Hereinafter, on the basis of information obtained by observing the two side-wall cores SC2 and SC3 acquired from the tectonic ground present at a predetermined depth from the earth's surface, three-dimensional stress elements acting on the tectonic ground from which the two cores are acquired will be obtained.

First, the degree of the vertical stress ($S_v$) can be obtained as an overburden pressure using the method in the first embodiment.

Next, a differential stress ($\Delta\sigma|\beta_2$) between the horizontal stress ($\sigma_\theta$) acting on the vicinity of the first measurement cross section when the side-wall core SC2 is present in the ground and the vertical stress ($\sigma_v$) that, similarly, acts on the vicinity of the first measurement cross section can be represented by equation (6) below in a case where stress concentration is taken into account. In equation (6), when the diameter ($d2a|_{\phi=0}$) in the vertical direction is shorter than the diameter ($d2a|_{\phi=90}$) in the horizontal direction, the length of the minimum diameter ($d_{min}$) of the first measurement cross section in the side-wall core SC2 is regarded as the length of the diameter ($d2a|_{\phi=0}$) in the vertical direction, and, when the diameter ($d2a|_{\phi=0}$) in the vertical direction is longer than the diameter ($d2a|_{\phi=90}$) in the horizontal direction, the length of the minimum diameter ($d_{min}$) of the first measurement cross section in the side-wall core SC2 is regarded as the length of the diameter ($d2a|_{\phi=90}$) in the horizontal direction.

$$\Delta\sigma|_{\beta_2, r=r_{2a}} = \qquad (6)$$

$$\frac{1}{2}(S_{Hmax}+S_{hmin})\left(1+\frac{R^2}{r_{2a}^2}\right)-(S_{Hmax}-S_{hmin})\left(\frac{1}{2}-2\nu\frac{R^2}{r_{2a}^2}+\frac{3R^4}{2r_{2a}^4}\right)$$

$$\cos 2(\beta_2-\alpha)-S_V = \frac{E}{1+\nu} \cdot \frac{d2a|_{\phi=90}-d2a|_{\phi=0}}{d_{min}}$$

In addition, the differential stress ($\Delta\sigma|\beta_2$) between the horizontal stress ($\sigma_\theta$) acting on the vicinity of the second measurement cross section when the side-wall core SC2 is present in the ground and the vertical stress ($\sigma_v$) that, similarly, acts on the vicinity of the second measurement cross section can be represented by equation (7) below in a case where stress concentration is taken into account. In equation (7), when the diameter ($d2b|_{\phi=0}$) in the vertical direction is shorter than the diameter ($d2b|_{\phi=90}$) in the horizontal direction, the length of the minimum diameter ($d_{min}$) of the second measurement cross section in the side-wall core SC2 is regarded as the length of the diameter ($d2|_{\phi=0}$) in the vertical direction, and, when the diameter ($d2b|_{\phi=0}$) in the vertical direction is longer than the diameter ($d2b|_{\phi=90}$) in the horizontal direction, the length of the minimum diameter ($d_{min}$) of the second measurement cross section in the side-wall core SC2 is regarded as the length of the diameter ($d2b|_{\phi=90}$) in the horizontal direction.

$$\Delta\sigma|_{\beta_2, r=r_{2b}} = \qquad (7)$$

$$\frac{1}{2}(S_{Hmax}+S_{hmin})\left(1+\frac{R^2}{r_{2b}^2}\right)-(S_{Hmax}-S_{hmin})\left(\frac{1}{2}-2\nu\frac{R^2}{r_{2b}^2}+\frac{3R^4}{2r_{2b}^4}\right)$$

$$\cos 2(\beta_2-\alpha)-S_V = \frac{E}{1+\nu} \cdot \frac{d2b|_{\phi=90}-d2b|_{\phi=0}}{d_{min}}$$

A differential stress ($\Delta\sigma|\beta_3$) between the horizontal stress ($\sigma_\theta$) acting on the vicinity of the third measurement cross section when the side-wall core SC3 is present in the ground and the vertical stress ($\sigma_v$) that, similarly, acts on the vicinity of the third measurement cross section can be represented by equation (8) below in a case where stress concentration is taken into account. In equation (8), when the diameter ($d3a|_{\phi=0}$) in the vertical direction is shorter than the diameter ($d3a|_{\phi=90}$) in the horizontal direction, the length of the minimum diameter ($d_{min}$) of the third measurement cross section in the side-wall core SC3 is regarded as the length of the diameter ($d3a|_{\phi=0}$) in the vertical direction, and, when the diameter ($d3a|_{\phi=0}$) in the vertical direction is longer than the diameter ($d3a|_{\phi=90}$) in the horizontal direction, the length of the minimum diameter ($d_{min}$) of the third measurement cross section in the side-wall core SC3 is regarded as the length of the diameter ($d3a|_{\phi=90}$) in the horizontal direction.

$$\Delta\sigma|_{\beta_3, r=r_{3a}} = \qquad (8)$$

$$\frac{1}{2}(S_{Hmax}+S_{hmin})\left(1+\frac{R^2}{r_{3a}^2}\right)-(S_{Hmax}-S_{hmin})\left(\frac{1}{2}-2\nu\frac{R^2}{r_{3a}^2}+\frac{3R^4}{2r_{3a}^4}\right)$$

$$\cos 2(\beta_3-\alpha)-S_V = \frac{E}{1+\nu} \cdot \frac{d3a|_{\phi=90}-d3a|_{\phi=0}}{d_{min}}$$

A differential stress ($\Delta\sigma|\beta_3$) between the horizontal stress ($\sigma_\theta$) acting on the vicinity of the fourth measurement cross section when the side-wall core SC3 is present in the ground and the vertical stress ($\sigma_v$) that, similarly, acts on the vicinity of the fourth measurement cross section can be represented by equation (9) below in a case where stress concentration is taken into account. In equation (9), when the diameter (d3 b$|_{\phi=0}$) in the vertical direction is shorter than the diameter (d3b$|_{\phi=90}$) in the horizontal direction, the length of the minimum diameter (d$_{min}$) of the fourth measurement cross section in the side-wall core SC3 is regarded as the length of the diameter (d3b$|_{\phi=0}$) in the vertical direction, and, when the diameter (d3b$|_{\phi=0}$) in the vertical direction is longer than the diameter (d3a$|_{\phi=90}$) in the horizontal direction, the length of the minimum diameter (d$_{min}$) of the fourth measurement cross section in the side-wall core SC3 is regarded as the length of the diameter (d3b$|_{\phi=90}$) in the horizontal direction.

$$\Delta\sigma|_{\beta_3, r=r_{3b}} = \qquad (9)$$

$$\frac{1}{2}(S_{Hmax} + S_{hmin})\left(1 + \frac{R^2}{r_{3b}^2}\right) - (S_{Hmax} - S_{hmin})\left(\frac{1}{2} - 2v\frac{R^2}{r_{3b}^2} + \frac{3R^4}{2r_{3b}^4}\right)$$

$$\cos 2(\beta_3 - \alpha) - S_V = \frac{E}{1+v} \cdot \frac{d3b|_{\phi=90} - d3b|_{\phi=0}}{d_{min}}$$

Angles ($\alpha$) formed by, among the three-dimensional stress elements, the remaining maximum horizontal stress ($S_{Hmax}$) and the direction in which the maximum horizontal stress ($S_{Hmax}$) and the minimum horizontal stress ($S_{hmin}$) act with respect to the standard orientation can be obtained using the equations (6), (7), (8), and (9) as simultaneous equations and, desirably, the non-linear least-square method.

According to the third embodiment of the in-situ stress measurement method of the present invention, it is possible to measure the degrees of the three-direction stresses acting on the tectonic ground at the predetermined depth by combining information obtained from the two side-wall cores SC2 and SC3 and evaluate the stress state of the tectonic ground on the basis of the combined information. Boring cores are acquired in fragments during the excavation of wells, and thus there is a case where there are no boring cores acquired at a depth at which main stresses need to be measured afterwards, but side-wall cores can be acquired at any depths as necessary after the excavation of wells. Therefore, according to the present embodiment, it is possible to measure the degrees of the three-direction stresses at any depths in the ground regardless of the presence or absence of boring cores, and it is possible to precisely acknowledge the properties of the tectonic ground with a high accuracy throughout the entire region. That is, according to the third embodiment, similar to the first embodiment, it becomes possible to efficiently mine underground fossil fuels such as petroleum and natural gas, and, furthermore, in a variety of projects for which the evaluation of stresses in rock grounds at a deep depth is significantly important, it becomes possible to accurately measure stresses in rock grounds by carrying out the present invention.

Fourth Embodiment

Next, a fourth embodiment of the in-situ stress measurement method according to the present invention will be described in detail with reference to FIG. 8. In some cases, matters that have been described in detail in the first, second, and third embodiments will be only simply described in the present embodiment.

In the present embodiment, on the basis of information obtained by observing three side-wall cores SC4, SC5, and SC6 acquired from the tectonic ground present at a predetermined depth from the earth's surface, three-dimensional stress elements acting on the tectonic ground from which the same cores have been acquired are obtained.

Figure 8:
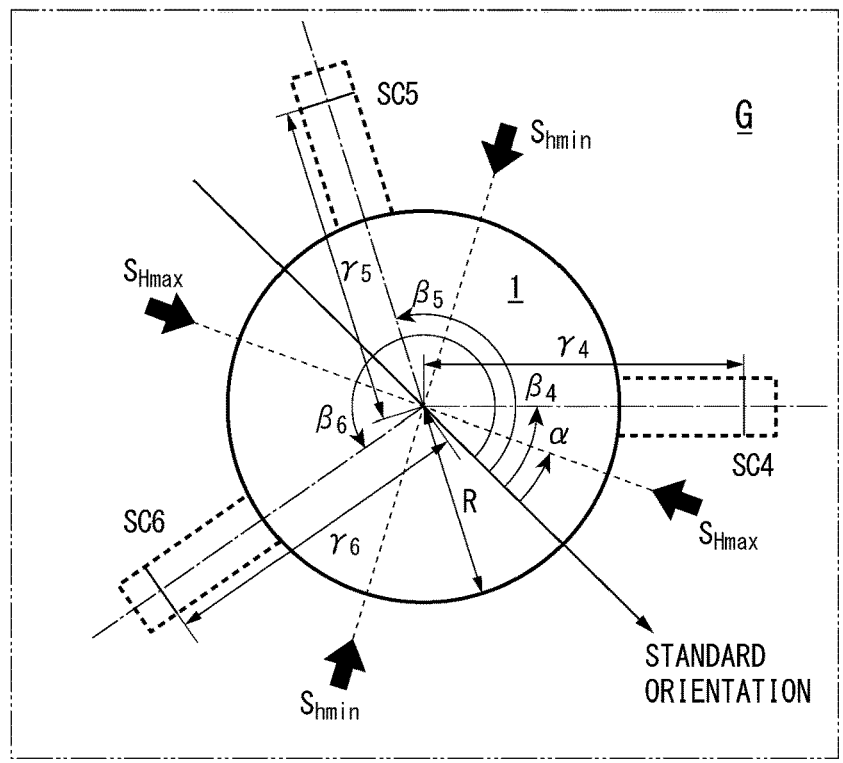
FIG. 8 is a view describing a fourth embodiment of the in-situ stress measurement method according to the present invention and a view schematically showing a status in which, among the three-dimensional stresses, the maximum horizontal stress ($S_{Hmax}$) and the minimum horizontal stress ($S_{hmin}$) act on the tectonic ground located at the predetermined depth from the earth's surface and showing locations of three side-wall cores that are to be acquired from the well.

First, as shown in FIG. 8, a cylindrical side-wall core (fourth side-wall core) SC4 is acquired by hollowing the ground out from an inside surface of a well at a predetermined depth from the earth's surface in a direction orthogonal to an excavation direction of the well, that is, a certain direction in a horizontal plane using the method in the first embodiment. It is needless to say that, on the ground from which the side-wall core SC4 has been acquired, the maximum horizontal stress ($S_{Hmax}$), the minimum horizontal stress ($S_{hmin}$), and the vertical stress ($S_v$) act, and thus, when the side-wall core SC4 is hollowed out from the ground and removed from the well, the cross-sectional shape of the side-wall core SC4 changes in the same manner as those of the side-wall cores SC1, SC2, and SC3.

A measurement cross section is set in the side-wall core SC4, and, similar to the third embodiment, the length of a diameter (d4$|_{\phi=0}$) of the measurement cross section in the vertical direction and the length of a diameter (d4$|_{\phi=90}$) in the horizontal direction are measured. When the measurement results are plotted in a graph, and an approximate curve is obtained using the least-square method or the like, the characteristics of the maximum value and the minimum value appear in the same manner as in the side-wall cores SC1, SC2, and SC3.

Next, a cylindrical side-wall core (fifth side-wall core) SC5 is acquired by hollowing the ground out from an inside surface of a well at a predetermined depth from the earth's surface that is the same as the depth at which the side-wall core SC4 is acquired in the horizontal direction different from the excavation direction of the side-wall core SC4. The cross-sectional shape of the side-wall core SC5 also changes in the same manner as that of the side-wall core SC4.

A measurement cross section is set in the side-wall core SC5, and the length of a diameter (d5$|_{\phi=0}$) of the measurement cross section in the vertical direction and the length of a diameter (d5$|_{\phi=90}$) in the horizontal direction are measured using the same method as described above. When the measurement results are plotted in a graph, and an approximate curve is obtained using the least-square method or the like, the characteristics of the maximum value and the minimum value appear in the same manner as in the side-wall core SC4.

Next, a cylindrical side-wall core (sixth side-wall core) SC6 is acquired by hollowing the ground out from an inside surface of a well at a predetermined depth from the earth's surface that is almost the same as the depth at which the side-wall cores SC4 and SC5 are acquired in the horizontal direction different from the excavation direction of the side-wall core SC4 and the excavation direction of the side-wall core SC5. The cross-sectional shape of the side-wall core SC6 also changes in the same manner as those of the side-wall cores SC4 and SC5.

A measurement cross section is set in the side-wall core SC6, and the length of a diameter (d6$|_{\phi=0}$) of the measurement cross section in the vertical direction and the length of a diameter (d6$|_{\phi=90}$) in the horizontal direction are measured using the same method as described above. When the measurement results are plotted in a graph, and an approximate curve is obtained using the least-square method or the like, the characteristics of the maximum value and the minimum value appear in the same manner as in the side-wall cores SC4 and SC5.

The excavation directions of the side-wall cores SC4, SC5, and SC6 can be specified by setting an angle formed by the excavation direction of the side-wall core SC4 with respect to the standard orientation of the well to ($\beta_4$), setting an angle formed by the excavation direction of the side-wall core SC5 with respect to the standard orientation of the well to ($\beta_5$), and, furthermore, setting an angle formed by the excavation direction of the side-wall core SC6 with respect to the standard orientation of the well to ($\beta_6$) using the method described in the first embodiment.

Hereinafter, on the basis of information obtained by observing the three side-wall cores SC4, SC5, and SC6 acquired from the tectonic ground present at a predetermined depth from the earth's surface, three-dimensional stress elements acting on the tectonic ground from which the three cores are acquired will be obtained.

First, the degree of the vertical stress ($S_V$) can be obtained as an overburden pressure using the method in the first embodiment.

Next, a differential stress ($\Delta\sigma|\beta_4$) between the horizontal stress ($\sigma_\theta$) acting on the vicinity of the measurement cross section when the side-wall core SC4 is present in the ground and the vertical stress ($\sigma_v$) that, similarly, acts on the vicinity of the measurement cross section can be represented by equation (10) below in a case where stress concentration is not taken into account. In equation (10), when the diameter ($d4|_{\phi=0}$) in the vertical direction is shorter than the diameter ($d4|_{\phi=90}$) in the horizontal direction, the length of the minimum diameter ($d_{min}$) of the measurement cross section in the side-wall core SC4 is regarded as the length of the diameter ($d4|_{\phi=0}$) in the vertical direction, and, when the diameter ($d4|_{\phi=0}$) in the vertical direction is longer than the diameter ($d4|_{\phi=90}$) in the horizontal direction, the length of the minimum diameter ($d_{min}$) of the measurement cross section in the side-wall core SC4 is regarded as the length of the diameter ($d4|_{\phi=90}$) in the horizontal direction.

$$\Delta\sigma|_{\beta_4} = \frac{1}{2}(S_{Hmax} + S_{hmin}) - \frac{1}{2}(S_{Hmax} - S_{hmin})\cos 2(\beta_4 - \alpha) - S_V = \frac{E}{1+v} \cdot \frac{d4|_{\phi=90} - d4|_{\phi=0}}{d_{min}} \quad (10)$$

Next, a differential stress ($\Delta\sigma|\beta_5$) between the horizontal stress ($\sigma_\theta$) acting on the vicinity of the measurement cross section when the side-wall core SC5 is present in the ground and the vertical stress ($\sigma_v$) that, similarly, acts on the vicinity of the measurement cross section can be represented by equation (11) below in a case where stress concentration is not taken into account. In equation (11), when the diameter ($d5|_{\phi=0}$) in the vertical direction is longer than the diameter ($d5|_{\phi=90}$) in the horizontal direction, the length of the minimum diameter ($d_{min}$) of the measurement cross section in the side-wall core SC5 is regarded as the length of the diameter ($d5|_{\phi=0}$) in the vertical direction, and, when the diameter ($d5|_{\phi=0}$) in the vertical direction is longer than the diameter ($d5|_{\phi=90}$) in the horizontal direction, the length of the minimum diameter ($d_{min}$) of the measurement cross section in the side-wall core SC5 is regarded as the length of the diameter ($d5|_{\phi=90}$) in the horizontal direction.

$$\Delta\sigma|_{\beta_5} = \frac{1}{2}(S_{Hmax} + S_{hmin}) - \frac{1}{2}(S_{Hmax} - S_{hmin})\cos 2(\beta_5 - \alpha) - S_V = \frac{E}{1+v} \cdot \frac{d5|_{\phi=90} - d5|_{\phi=0}}{d_{min}} \quad (11)$$

Next, a differential stress ($\Delta\sigma|\beta_6$) between the horizontal stress ($\sigma_\theta$) acting the vicinity of the measurement cross section when the side-wall core SC6 is present in the ground and the vertical stress ($\sigma_v$) that, similarly, acts on the vicinity of the measurement cross section can be represented by equation (12) below in a case where stress concentration is not taken into account. In equation (11), when the diameter ($d6|_{\phi=0}$) in the vertical direction is shorter than the diameter ($d6|_{\phi=0}$) in the horizontal direction, the length of the minimum diameter ($d_{min}$) of the measurement cross section in the side-wall core SC6 is regarded as the length of the diameter ($d6|_{\phi=0}$) in the vertical direction, and, when the diameter ($d6|_{\phi=0}$) in the vertical direction is longer than the diameter ($d6|_{\phi=90}$) in the horizontal direction, the length of the minimum diameter ($d_{min}$) of the measurement cross section in the side-wall core SC6 is regarded as the length of the diameter ($d6|_{\phi=90}$) in the horizontal direction.

$$\Delta\sigma|_{\beta_6} = \frac{1}{2}(S_{Hmax} + S_{hmin}) - \frac{1}{2}(S_{Hmax} - S_{hmin})\cos 2(\beta_6 - \alpha) - S_V = \frac{E}{1+v} \cdot \frac{d5|_{\phi=90} = d5|_{\phi=0}}{d_{min}} \quad (12)$$

Angles ($\alpha$) formed by, among the three-dimensional stress elements, the remaining maximum horizontal stress ($S_{Hmax}$) and the direction in which the maximum horizontal stress ($S_{Hmax}$) and the minimum horizontal stress ($S_{hmin}$) act with respect to the standard orientation can be obtained using the equations (10), (11), and (12) as simultaneous equations and, desirably, the solution of a non-linear simultaneous equations.

According to the fourth embodiment of the in-situ stress measurement method of the present invention, it is possible to measure the degrees of the three-direction stresses acting on the tectonic ground at the predetermined depth by combining information obtained from the three side-wall cores SC4, SC5, and SC6 and evaluate the stress state of the tectonic ground on the basis of the combined information. Boring cores are acquired in fragments during the excavation of wells, and thus there is a case where there are no boring cores acquired at a depth at which main stresses need to be measured afterwards, but side-wall cores can be acquired at any depths as necessary after the excavation of wells. Therefore, according to the present embodiment, it is possible to measure the degrees of the three-direction stresses at any depths in the ground regardless of the presence or absence of boring cores, and it is possible to precisely acknowledge the properties of the tectonic ground with a high accuracy throughout the entire region. That is, according to the fourth embodiment, similar to the first embodiment, it becomes possible to efficiently mine underground fossil fuels such as petroleum and natural gas, and, furthermore, in a variety of projects for which the evaluation of stresses in rock grounds at a deep depth is significantly important, it becomes possible to accurately measure stresses in rock grounds by carrying out the present invention.

Hitherto, the preferred embodiments of the present invention have been described in detail, but the present invention is not limited to such specific embodiments and can be modified in diverse forms within the scope of the gist of the present invention.

INDUSTRIAL APPLICABILITY

The present invention relates to an in-situ stress measurement method for measuring three-dimensional stress elements acting on the ground configuring the earth's crust. According to the present invention, it is possible to precisely measure three-dimensional stress elements acting on the ground at any depths.

REFERENCE SIGNS LIST

G TECTONIC GROUND
1 MAIN WELL (WELL)
BC1 BORING CORE
SC1 TO SC6 SIDE-WALL CORE

The invention claimed is:

1. An in-situ stress measurement method for measuring three-dimensional stress elements acting on ground configuring the earth's crust, the method comprising:
excavating the ground to form a well;
acquiring a cylindrical boring core by hollowing a portion of the ground in the well located at a predetermined depth from the earth's surface out in an excavation direction of the well during the excavation of the well;
specifying a first angle ($\alpha$) formed by an action direction of the maximum horizontal stress acting on the ground with respect to a standard orientation, which is an orientation of the maximum horizontal stress acting on the ground;
acquiring a cylindrical first side-wall core by hollowing the ground in the well located at the predetermined depth out from an inside surface of the well in a direction which is formed at a second angle ($\beta_1$) with respect to the standard orientation;
measuring a length of a maximum diameter ($D_{max}$) at which an amount of distortion relative to a diameter of a standard circle of a measurement cross section of the boring core is largest and a length of a minimum diameter ($D_{min}$) at which the amount of distortion relative to the diameter of the standard circle is smallest based on a shape of the measurement cross section of the boring core, wherein the measurement cross section of the boring core is set in a direction orthogonal to a longitudinal direction of the boring core;
measuring a length of a diameter ($d1|_{\phi=0}$) in a vertical direction of a measurement cross section of the first side-wall core and a length of a diameter ($d1|_{\phi=90}$) in a horizontal direction of the measurement cross section of the first side-wall core based on a shape of the measurement cross section of the first side-wall core, wherein the measurement cross section of the first side-wall core is set in a direction orthogonal to a longitudinal direction of the first side-wall core; and
calculating a maximum horizontal stress ($S_{Hmax}$) and a minimum horizontal stress ($S_{hmin}$) among the three-dimensional stress elements by first and second equations, wherein the first equation represents a differential stress ($\Delta S$) between a maximum horizontal stress ($S_{Hmax}$) and a minimum horizontal stress ($S_{hmin}$) acting on the ground at the predetermined depth, $$\Delta S = S_{Hmax} - S_{hmin} = \frac{E}{1+\nu} \cdot \frac{D_{max} - D_{min}}{D_{min}}$$

wherein the second equation represents a differential stress ($\Delta\sigma|_{\beta_1}$) between a horizontal stress ($\sigma_\theta$) and a vertical stress ($\sigma_V$) that act orthogonal to the longitudinal direction of the first side-wall core, $$\Delta\sigma|_{\beta_1} = \frac{1}{2}(S_{Hmax} + S_{hmin}) - \frac{1}{2}(S_{Hmax} - S_{hmin})\cos 2(\beta_1 - \alpha) - S_V$$
$$= \frac{E}{1+\nu} \cdot \frac{d1|_{\phi=90} - d1|_{\phi=0}}{d_{min}}$$

where degrees of variables below are regarded as being already known:
E: Young's modulus of the ground, $\nu$: Poisson's ratio of the ground, and
$S_V$: a vertical stress acting on the ground at the predetermined depth,
where $d_{min}=d1|_{\phi=0}$ when $d1|_{\phi=0}<d1|_{\phi=90}$, and $d_{min}=d1|_{\phi=90}$ when $d1|_{\phi=0}>d1|_{\phi=90}$.

2. The in-situ stress measurement method according to claim 1, wherein an angle formed by the standard orientation and a direction of the maximum diameter ($D_{max}$) in the measurement cross section of the boring core is regarded as the angle ($\alpha$) formed by the action direction of the maximum horizontal stress acting on the ground with respect to the standard orientation.

3. An in-situ stress measurement method for measuring three-dimensional stress elements acting on ground configuring the earth's crust, the method comprising:
excavating the ground to form a well in radius (R);
acquiring a cylindrical boring core by hollowing a portion of the ground in the well located at a predetermined depth from the earth's surface out in an excavation direction of the well during the excavation of the well;
specifying a first angle ($\alpha$) formed by an action direction of the maximum horizontal stress acting on the ground with respect to a standard orientation, which is an orientation of the maximum horizontal stress acting on the ground;
acquiring a cylindrical first side-wall core by hollowing the ground in the well located at the predetermined depth out from an inside surface of the well in a direction which is formed at a second angle ($\beta_1$) with respect to the standard orientation;
measuring a length of a maximum diameter ($D_{max}$) at which an amount of distortion relative to a diameter of a standard circle of a measurement cross section of the boring core is largest and a length of a minimum diameter ($D_{min}$) at which the amount of distortion relative to the diameter of the standard circle is smallest based on a shape of the measurement cross section of the boring core, wherein the measurement cross section of the boring core is set in a direction orthogonal to a longitudinal direction of the boring core;
measuring a length of a diameter ($d1|_{\phi=0}$) in a vertical direction of a measurement cross section of the first side-wall core and a length of a diameter ($d1|_{\phi=90}$) in a horizontal direction of the measurement cross section of the first side-wall core based on a shape of the measurement cross section of the first side-wall core, wherein the measurement cross section of the first side-wall core is set in a direction orthogonal to a longitudinal direction of the first side-wall core; and calculating a maximum horizontal stress ($S_{Hmax}$) and a minimum horizontal stress ($S_{hmin}$) among the three-dimensional stress elements by first and second equations, wherein the first equation represents a differential stress ($\Delta S$) between a maximum horizontal stress ($S_{Hmax}$) and a minimum horizontal stress ($S_{hmin}$) acting on the ground at the predetermined depth, $$\Delta S = S_{Hmax} - S_{hmin} = \frac{E}{1+v} \cdot \frac{D_{max} - D_{min}}{D_{min}}$$

wherein the second equation represents a differential stress ($\Delta\sigma|\beta_1$) between a horizontal stress ($\sigma_\theta$) and a vertical stress ($\sigma_v$) that act orthogonal to the longitudinal direction of the first side-wall core, $$\Delta\sigma|\beta_1 = \frac{1}{2}(S_{Hmax} + S_{hmin})\left(1 + \frac{R^2}{r_1^2}\right) -$$
$$(S_{Hmax} - S_{hmin})\left(\frac{1}{2} - 2v\frac{R^2}{r_1^2} + \frac{3R^4}{2r_1^4}\right)$$
$$\cos 2(\beta_1 - \alpha) - S_V$$
$$= \frac{E}{1+v} \cdot \frac{d1'|_{\phi=90} - d1|_{\phi=0}}{d_{min}}$$

where degrees of variables below are regarded as being already known:

E: Young's modulus of the ground, v: Poisson's ratio of the ground, and $S_v$: a vertical stress acting on the ground at the predetermined depth, $r_1$: a distance from a center of the well to the measurement cross section of the first side-wall core, where $d_{min}=d1'|_{\phi=0}$ when $d1'|_{\phi=0}<d1'|_{\phi=90}$, and $d_{min}=d1'|_{\phi=90}$ when $d1'|_{\phi=0}>d1'|_{\phi=90}$.

4. The in-situ stress measurement method according to claim 3, wherein an angle formed by the standard orientation and a direction of the maximum diameter ($D_{max}$) in the measurement cross section of the boring core is regarded as the angle ($\alpha$) formed by the action direction of the maximum horizontal stress acting on the ground with respect to the standard orientation.

5. An in-situ stress measurement method for measuring three-dimensional stress elements acting on ground configuring the earth's crust, the method comprising:

excavating the ground to form a well;

specifying a first angle ($\alpha$) formed by an action direction of the maximum horizontal stress acting on the ground with respect to a standard orientation, which is an orientation of the maximum horizontal stress acting on the ground, during the excavation of the well;

acquiring a cylindrical first side-wall core by hollowing the ground in the well located at the predetermined depth out from an inside surface of the well in a direction which is formed at a second angle ($\beta_1$) with respect to the standard orientation;

measuring a length of a diameter ($d1|_{\phi=0}$) in a vertical direction of a measurement cross section of the first side-wall core and a length of a diameter ($d1|_{\phi=90}$) in a horizontal direction of the measurement cross section of the first side-wall core based on a shape of the measurement cross section of the first side-wall core, wherein the measurement cross section is set in a direction orthogonal to a longitudinal direction of the first side-wall core; and calculating a maximum horizontal stress ($S_{Hmax}$) acting on the ground at the predetermined depth among the three-dimensional stress elements by an equation which represents a differential stress ($\Delta\sigma|\beta_1$) between a horizontal stress ($\sigma_\theta$) and a vertical stress ($\sigma_v$) that act orthogonal to the longitudinal direction of the first side-wall core, $$\Delta\sigma|\beta_1 = \frac{1}{2}(S_{Hmax} + S_{Hmin}) -$$
$$\frac{1}{2}(S_{Hmax} - S_{hmin})\cos 2(\beta_1 - \alpha) - S_V$$
$$= \frac{E}{1+v} \cdot \frac{d1|_{\phi=90} - d1|_{\phi=0}}{d_{min}}$$

where degrees of variables below are regarded as being already known:

E: Young's modulus of the ground, v: Poisson's ratio of the ground, $S_v$: a vertical stress acting on the ground at the predetermined depth, and $S_{hmin}$: a minimum horizontal stress acting on the ground at the predetermined depth, where $d_{min}=d1|_{\phi=0}$ when $d1|_{\phi=0}<d1|_{\phi=90}$, and $d_{min}=d1|_{\phi=90}$ when $d1|_{\phi=0}>d1|_{\phi=90}$.

6. An in-situ stress measurement method for measuring three-dimensional stress elements acting on ground configuring the earth's crust, the method comprising:

excavating the ground to form a well in radius (R);

specifying a first angle ($\alpha$) formed by an action direction of the maximum horizontal stress acting on the ground with respect to a standard orientation, which is an orientation of the maximum horizontal stress acting on the ground, during the excavation of the well;

acquiring a cylindrical first side-wall core by hollowing the ground in the well located at the predetermined depth out from an inside surface of the well in a direction which is formed at a second angle ($\beta_1$) with respect to the standard orientation;

measuring a length of a diameter ($d1|_{\phi=0}$) in a vertical direction of a measurement cross section of the first side-wall core and a length of a diameter ($d1|_{\phi=90}$) in a horizontal direction of the measurement cross section of the first side-wall core based on a shape of the measurement cross section of the first side-wall core, wherein the measurement cross section is set in a direction orthogonal to a longitudinal direction of the first side-wall core; and calculating a maximum horizontal stress ($S_{Hmax}$) acting on the ground at the predetermined depth among the three-dimensional stress elements by an equation which represents a differential stress ($\Delta\sigma|\beta_1$) between a horizontal stress ($\sigma_\theta$) and a vertical stress ($\sigma_v$) that act orthogonal to the longitudinal direction of the first side-wall core, $$\Delta\sigma|_{\beta_1,r=r_1} = \frac{1}{2}(S_{Hmax} + S_{hmin})\left(1 + \frac{R^2}{r_1^2}\right) -$$
$$(S_{Hmax} - S_{hmin})\left(\frac{1}{2} - 2v\frac{R^2}{r_1^2} + \frac{3R^4}{2r_1^4}\right)$$
$$\cos 2(\beta_1 - \alpha) - S_V$$
$$= \frac{E}{1+v} \cdot \frac{d1|_{\phi=90} - d1'|_{\phi=0}}{d_{min}}$$

where degrees of variables below are regarded as being already known:
E: Young's modulus of the ground, v: Poisson's ratio of the ground,
$S_v$: a vertical stress acting on the ground at the predetermined depth,
$S_{hmin}$: a minimum horizontal stress acting on the ground at the predetermined depth,
$r_1$: a distance from a center of the well to the measurement cross section of the first side-wall core,
where $d_{min}=d1|_{\phi=0}$ when $d1|_{\phi=0}<d1|_{\phi=90}$, and $d_{min}=d1|_{\phi=90}$ when $d1|_{\phi=0}>d1|_{\phi=90}$.

7. An in-situ stress measurement method for measuring three-dimensional stress elements acting on ground configuring the earth's crust, the method comprising:
excavating the ground to form a well in radius (R);
specifying a first angle (α) formed by an action direction of the maximum horizontal stress acting on the ground with respect to a standard orientation, which is an orientation of the maximum horizontal stress acting on the ground, during the excavation of the well;
acquiring a cylindrical first side-wall core by hollowing the ground in the well located at the predetermined depth from the earth's surface out from an inside surface of the well in a direction which is formed at a second angle ($\beta_2$) with respect to the standard orientation;
acquiring a cylindrical second side-wall core by hollowing the ground in the well located at the predetermined depth from the earth's surface out from the inside surface of the well in a direction which is formed at a third angle ($\beta_3$) with respect to the standard orientation, which is different from an excavation direction of the well and an excavation direction of the first side-wall core;
measuring a length of a diameter (d2a|$_{\phi=0}$) in a vertical direction of a first measurement cross section of the first side-wall core and a length of a diameter (d2a|$_{\phi=90}$) in a horizontal direction of the first measurement cross section of the first side-wall core based on a shape of the first measurement cross section of the first side-wall core, wherein the first measurement cross section of the first side-wall core is set in a direction orthogonal to a longitudinal direction of the first side-wall core;
measuring a length of a diameter (d2b|$_{\phi=0}$) the vertical direction of a second measurement cross section of the second side-wall core and a length of a diameter (d2b|$_{\phi=90}$) in the horizontal direction of the second measurement cross section of the first side-wall core, wherein the second measurement cross section of the second side-wall core is different from the first measurement cross section;
measuring a length of a diameter (d3a|$_{\phi=0}$) in the vertical direction of a third measurement cross section of the second side-wall core and a length of a diameter (d3a|$_{\phi=90}$) in the horizontal direction of the third measurement cross section of the second side-wall core based on a shape of the third measurement cross section of the second side-wall core, wherein the third measurement cross section is set in a direction orthogonal to the longitudinal direction of the second side-wall core;
measuring a length of a diameter (d3b|$_{\phi=0}$) in the vertical direction of a fourth measurement cross section of the second side-wall core and a length of a diameter (d3b|$_{\phi=90}$) in the horizontal direction of the fourth measurement cross section of the second side-wall core, wherein the fourth measurement cross section of the second side-wall core is different from the third measurement cross section; and,
calculating a maximum horizontal stress ($S_{Hmax}$) and a minimum horizontal stress ($S_{hmin}$) acting on the ground at the predetermined depth and an angle (α) formed by the action direction of the maximum horizontal stress with respect to the standard orientation that is an orientation of the maximum horizontal stress acting on the ground by first, second, third and fourth equations, wherein the first equation represents a differential stress ($\Delta\sigma|_{\beta_2}$) between a horizontal stress ($\sigma_\theta$) and a vertical stress ($\sigma_v$) in the first measurement cross section of the first side-wall core, $$\Delta\sigma|_{\beta_2,r=r_{2a}} = \frac{1}{2}(S_{Hmax} + S_{hmin})\left(1 + \frac{R^2}{r_{2a}^2}\right) -$$
$$(S_{Hmax} - S_{hmin})\left(\frac{1}{2} - 2v\frac{R^2}{r_{2a}^2} + \frac{3R^4}{2r_{2a}^4}\right)$$
$$\cos 2(\beta_2 - \alpha) - S_V$$
$$= \frac{E}{1+v} \cdot \frac{d2a|_{\phi=90} - d2a|_{\phi=0}}{d_{min}}$$

wherein the second equation represents the differential stress ($\Delta\sigma|_{\beta_2}$) between the horizontal stress ($\sigma_\theta$) and the vertical stress ($\sigma_v$) in the second measurement cross section of the first side-wall core, $$\Delta\sigma|_{\beta_2,r=r_{2b}} = \frac{1}{2}(S_{Hmax} + S_{hmin})\left(1 + \frac{R^2}{r_{2b}^2}\right) -$$
$$(S_{Hmax} - S_{hmin})\left(\frac{1}{2} - 2v\frac{R^2}{r_{2b}^2} + \frac{3R^4}{2r_{2b}^4}\right)$$
$$\cos 2(\beta_2 - \alpha) - S_V$$
$$= \frac{E}{1+v} \cdot \frac{d2b|_{\phi=90} - d2b|_{\phi=0}}{d_{min}}$$

wherein the third equation represents a differential stress ($\Delta\sigma|_{\beta_3}$) between the horizontal stress ($\sigma_\theta$) and the vertical stress ($\sigma_v$) in the third measurement cross section of the second side-wall core, and $$\Delta\sigma|_{\beta_3,r=r_{3a}} = \frac{1}{2}(S_{Hmax} + S_{hmin})\left(1 + \frac{R^2}{r_{3a}^2}\right) -$$
$$(S_{Hmax} - S_{hmin})\left(\frac{1}{2} - 2v\frac{R^2}{r_{3a}^2} + \frac{3R^4}{2r_{3a}^4}\right)$$
$$\cos 2(\beta_3 - \alpha) - S_V$$
$$= \frac{E}{1+v} \cdot \frac{d3a|_{\phi=90} - d3a|_{\phi=0}}{d_{min}}$$

wherein the fourth equation represents the differential stress ($\Delta\sigma|_{\beta_3}$) between the horizontal stress ($\sigma_\theta$) and the vertical stress ($\sigma_V$) in the fourth measurement cross section of the second side-wall core, $$\Delta\sigma|_{\beta_3, r=r_{3b}} = \frac{1}{2}(S_{Hmax} + S_{hmin})\left(1 + \frac{R^2}{r_{3b}^2}\right) -$$
$$(S_{Hmax} - S_{hmin})\left(\frac{1}{2} - 2v\frac{R^2}{r_{3b}^2} + \frac{3R^4}{2r_{3b}^4}\right)$$
$$\cos 2(\beta_3 - \alpha) - S_V$$
$$= \frac{E}{1+v} \cdot \frac{d3b|_{\phi=90} - d3b|_{\phi=0}}{d_{min}}$$

where degrees of variables below are regarded as being already known:
E: Young's modulus of the ground, v: Poisson's ratio of the ground,
$S_v$: a vertical stress acting on the ground at the predetermined depth,
$r_{2a}$: a distance from a center of the well to the first measurement cross section of the first side-wall core,
$r_{2b}$: a distance from the center of the well to the second measurement cross section of the first side-wall core,
$r_{3a}$: a distance from the center of the well to the third measurement cross section of the second side-wall core, and
$r_{3b}$: a distance from the center of the well to the fourth measurement cross section of the second side-wall core,
where $d_{min}$=d2a|$_{\phi=0}$ when d2a|$_{\phi=0}$<d2a|$_{\phi=90}$, and $d_{min}$=d2a|$_{\phi=90}$ when d2a|$_{\phi=0}$>d2a|$_{\phi=90}$,
in equation, $d_{min}$=d2b|$_{\phi=0}$ when d2b|$_{\phi=0}$<d2b|$_{\phi=90}$, and $d_{min}$=d2b|$_{\phi=90}$ when d2a|$_{\phi=0}$>d2a|$_{\phi=90}$,
in equation, $d_{min}$=d3a|$_{\phi=0}$ when d3a|$_{\phi=0}$<d3a|$_{\phi=90}$, and $d_{min}$=d3|$_{\phi=90}$ when d3a|$_{\phi=0}$<d3a|$_{\phi=90}$, and
in equation, $d_{min}$=d3b|$_{\phi=0}$ when d3b|$_{\phi=0}$<d3b|$_{\phi=90}$, and $d_{min}$=d3b|$_{\phi=90}$ when d3b|$_{\phi=0}$>d3b|$_{\phi=90}$.

8. An in-situ stress measurement method for measuring three-dimensional stress elements acting on ground configuring the earth's crust, the method comprising:
excavating the ground to form a well;
specifying a first angle ($\alpha$) formed by an action direction of the maximum horizontal stress with respect to a standard orientation, which is an orientation of the maximum horizontal stress acting on the ground, during excavation of the well;
acquiring a cylindrical first side-wall core by hollowing the ground in the well located at the predetermined depth from the earth's surface out from an inside surface of the well in a direction which is formed at a second angle ($\beta_4$) with respect to the standard orientation;
acquiring a cylindrical second side-wall core by hollowing the ground in the well located at the predetermined depth from the earth's surface out from the inside surface of the well in a direction which is formed at a third angle ($\beta_5$) with respect to the standard orientation, which is different from an excavation direction of the well and an excavation direction of the first side-wall core;
acquiring a cylindrical third side-wall core by hollowing the ground in the well located at the predetermined depth from the earth's surface out from the inside surface of the well in a direction which is formed at a fourth angle ($\beta_6$) with respect to the standard orientation, which is different from the excavation direction of the well and excavation directions of the first and second side-wall cores;
measuring a length of a diameter (d4|$_{\phi=0}$) in a vertical direction of a measurement cross section of a cylindrical fourth the first side-wall core and a length of a diameter (d4|$_{\phi=90}$) in a horizontal direction of the measurement cross section of the first side-wall core based on a shape of the measurement cross section of the first side-wall core, wherein the measurement cross section of the first side-wall core is set in a direction orthogonal to a longitudinal direction of the first side-wall core;
measuring a length of a diameter (d5|$_{\phi=0}$) in the vertical direction a measurement cross section of the second side-wall core and a length of a diameter (d5|$_{\phi=90}$) in the horizontal direction of the measurement cross section of the second side-wall core based on a shape of the measurement cross section of the second side-wall core, wherein the measurement cross section of the second side-wall core is set in a direction orthogonal to the longitudinal direction of the second side-wall core;
measuring a length of a diameter (d6|$_{\phi=0}$) in the vertical direction of a measurement cross section of the third side-wall core and a length of a diameter (d6|$_{\phi=90}$) in the horizontal direction of the measurement cross section of the third side-wall core based on a shape of the measurement cross section of the third side-wall core, wherein the measurement cross section of the third side-wall core is set in a direction orthogonal to the longitudinal direction of the third side-wall core; and
calculating a maximum horizontal stress ($S_{Hmax}$) and a minimum horizontal stress ($S_{hmin}$) acting on the ground at the predetermined depth and an angle ($\alpha$) formed by the action direction of the maximum horizontal stress with respect to the standard orientation, that is an orientation of the maximum horizontal stress acting on the ground by first, second and third equations, wherein the first equation represents a differential stress ($\Delta\sigma|_{\beta_4}$) between a horizontal stress ($\sigma_\theta$) and a vertical stress ($\sigma_v$) in the measurement cross section of the first side-wall core, $$\Delta\sigma|_{\beta_4} = \frac{1}{2}(S_{Hmax} + S_{hmin}) -$$
$$\frac{1}{2}(S_{Hmax} - S_{hmin})\cos 2(\beta_4 - \alpha) - S_V$$
$$= \frac{E}{1+v} \cdot \frac{d4|_{\phi=90} - d4|_{\phi=0}}{d_{min}}$$

wherein the second equation represents the differential stress ($\Delta\sigma|_{\beta_5}$) between the horizontal stress ($\sigma_\theta$) and the vertical stress ($\sigma_v$) in the measurement cross section of the second side-wall core, and $$\Delta\sigma|_{\beta_5} = \frac{1}{2}(S_{Hmax} + S_{hmin}) -$$
$$\frac{1}{2}(S_{Hmax} - S_{hmin})\cos 2(\beta_5 - \alpha) - S_V$$
$$= \frac{E}{1+v} \cdot \frac{d5|_{\phi=90} - d5|_{\phi=0}}{d_{min}}$$

wherein the third equation represents a differential stress ($\Delta\sigma|_{\beta_6}$) between the horizontal stress ($\sigma_\theta$) and the vertical stress ($\sigma_v$) in the measurement cross section of the third side-wall core, $$\Delta\sigma\,|_{\beta_6} = \frac{1}{2}(S_{Hmax} + S_{hmin}) - \frac{1}{2}(S_{Hmax} - S_{hmin})\cos 2(\beta_6 - \alpha) - S_V$$
$$= \frac{E}{1+v} \cdot \frac{d6\,|_{\phi=90} - d6\,|_{\phi=0}}{d_{min}}$$

where degrees of variables below are regarded as being already known:

E: Young's modulus of the ground, v: Poisson's ratio of the ground, and $S_v$: a vertical stress acting on the ground at the predetermined depth, where $d_{min} = d4\,|_{\phi=0}$ when $d4\,|_{\phi=90}$, and $d_{min} = d4\,|_{\phi=90}$ when $d4\,|_{\phi=90}$, $d_{min} = d5\,|_{\phi=0}$ when $d5\,|_{\phi=0} < d5\,|_{\phi=90}$, and $d_{min} = d5\,|_{\phi=90}$ when $d5\,|_{\phi=0} > d5\,|_{\phi=90}$, and $d_{min} = d6\,|_{\phi=0}$ when $d6\,|_{\phi=0} < d6\,|_{\phi=90}$, and $d_{min} = d6\,|_{\phi=90}$ when $d6\,|_{\phi=0} > d6\,|_{\phi=90}$.

\* \* \* \* \*